(12) United States Patent
Ishida et al.

(10) Patent No.: US 11,668,024 B2
(45) Date of Patent: Jun. 6, 2023

(54) POLAR SOLVENT SOLUTION AND PRODUCTION METHOD THEREOF

(71) Applicant: SPIBER INC., Tsuruoka (JP)

(72) Inventors: Kana Ishida, Yamagata (JP); Hironori Yamamoto, Yamagata (JP); Hiroaki Suzumura, Yamagata (JP); Kazuhide Sekiyama, Yamagata (JP)

(73) Assignee: SPIBER, INC., Yamagata (JP)

( * ) Notice: Subject to any disclaimer, the term of this patent is extended or adjusted under 35 U.S.C. 154(b) by 25 days.

(21) Appl. No.: 16/740,106

(22) Filed: Jan. 10, 2020

(65) Prior Publication Data

US 2020/0131671 A1 Apr. 30, 2020

Related U.S. Application Data

(62) Division of application No. 15/564,142, filed as application No. PCT/JP2016/061025 on Apr. 4, 2016, now abandoned.

(30) Foreign Application Priority Data

Apr. 9, 2015 (JP) ................................ 2015-080226

(51) Int. Cl.
*D01F 4/02* (2006.01)
*D01C 3/00* (2006.01)
(Continued)

(52) U.S. Cl.
CPC .............. *D01F 4/02* (2013.01); *C07K 14/435* (2013.01); *C07K 14/43518* (2013.01); *D01C 3/00* (2013.01); *D01F 1/02* (2013.01)

(58) Field of Classification Search
None
See application file for complete search history.

(56) References Cited

U.S. PATENT DOCUMENTS

| 5,171,505 A | 12/1992 | Lock |
| 5,252,284 A | 10/1993 | Lock |

(Continued)

FOREIGN PATENT DOCUMENTS

| CN | 1078509 | 11/1993 |
| CN | 1774241 | 5/2006 |

(Continued)

OTHER PUBLICATIONS

Office Action issued in corresponding Chinese Patent Application No. 201680020745.1, dated Aug. 5, 2020, 25 pages with translation.

(Continued)

*Primary Examiner* — Joseph D Anthony
(74) *Attorney, Agent, or Firm* — Hamre, Schumann, Mueller & Larson, P.C.

(57) ABSTRACT

A polar solvent solution of the present invention is a polar solvent solution in which a solute containing a polyamine acid is dissolved in a polar solvent. The solution has a moisture content of less than 5 mass % based on 100 mass % of the solution. A method for producing a polar solvent solution of the present invention includes changing a moisture content of the solution to adjust the viscosity of the solution. Further, another method for producing a polar solvent solution includes reducing a moisture content of the solution to increase the viscosity of the solution. Thus, the present invention provides a polar solvent solution that enables stable spinning and casting without lowering its viscosity when used as dopes for spinning, film, etc., and methods for producing the same.

12 Claims, 3 Drawing Sheets

Specification includes a Sequence Listing.

(51) Int. Cl.
  C07K 14/435    (2006.01)
  D01F 1/02      (2006.01)

(56) References Cited

U.S. PATENT DOCUMENTS

| | | | |
|---|---|---|---|
| 5,736,586 | A | 4/1998 | Bastioli et al. |
| 6,620,917 | B1 | 9/2003 | Mello et al. |
| 7,014,802 | B1 | 3/2006 | Eby et al. |
| 7,057,023 | B2 | 6/2006 | Islam et al. |
| 7,335,739 | B2 | 2/2008 | Mello et al. |
| 8,278,416 | B1 | 10/2012 | Johansson et al. |
| 8,568,637 | B2 | 10/2013 | Gazit et al. |
| 9,051,453 | B2 * | 6/2015 | Sugahara ............ D01D 5/04 |
| 9,689,089 | B2 * | 6/2017 | Ishikawa ............ D01F 4/00 |
| 10,975,206 | B2 * | 4/2021 | Ishida ............ C07K 14/435 |
| 2003/0155670 | A1 | 8/2003 | O'Brien |
| 2003/0201560 | A1 | 10/2003 | Vollrath et al. |
| 2004/0102614 | A1 | 5/2004 | Islam et al. |
| 2004/0132957 | A1 | 7/2004 | Asakura |
| 2004/0161382 | A1 | 8/2004 | Yum et al. |
| 2005/0054830 | A1 | 3/2005 | Islam et al. |
| 2005/0158821 | A1 | 7/2005 | Mello et al. |
| 2007/0092558 | A1 | 4/2007 | Heavner et al. |
| 2009/0226969 | A1 | 9/2009 | Johansson et al. |
| 2009/0318963 | A1 | 12/2009 | Asakura |
| 2010/0113621 | A1 | 5/2010 | Hayashi et al. |
| 2011/0046686 | A1 | 2/2011 | Kaplan et al. |
| 2011/0136669 | A1 | 6/2011 | Liebmann et al. |
| 2012/0329992 | A1 | 12/2012 | Johansson et al. |
| 2013/0172478 | A1 | 7/2013 | Bausch |
| 2014/0058066 | A1 | 2/2014 | Sekiyama et al. |
| 2014/0245923 | A1 | 9/2014 | Sugahara et al. |
| 2015/0151264 | A1 | 6/2015 | Baseeth et al. |
| 2015/0291673 | A1 * | 10/2015 | Sekiyama ........ C07K 14/43518 530/353 |
| 2015/0361144 | A1 * | 12/2015 | Osawa ............ A61K 8/64 514/773 |
| 2018/0127553 | A1 * | 5/2018 | Ishida ............ C08J 3/097 |

FOREIGN PATENT DOCUMENTS

| | | |
|---|---|---|
| CN | 1952225 | 4/2007 |
| CN | 101139501 | 3/2008 |
| CN | 101564914 | 10/2009 |
| CN | 101705559 | 5/2010 |
| CN | 101721739 | 6/2010 |
| CN | 101724920 | 6/2010 |
| CN | 102181948 | 9/2011 |
| CN | 103126974 | 6/2013 |
| CN | 103184570 | 7/2013 |
| CN | 103827139 | 5/2014 |
| CN | 104428124 | 3/2015 |
| EP | 0559725 | 9/1993 |
| EP | 0816505 | 1/1998 |
| EP | 1 038 908 | 9/2000 |
| EP | 2 774 934 | 9/2014 |
| EP | 2 940 032 | 11/2015 |
| EP | 2 990 062 | 3/2016 |
| EP | 2 990 414 | 3/2016 |
| JP | 02-240165 | 9/1990 |
| JP | 4-263614 | 9/1992 |
| JP | 5-263312 | 10/1993 |
| JP | 6-502993 | 4/1994 |
| JP | 8-74123 | 3/1996 |
| JP | 11-217506 | 8/1999 |
| JP | 2004-503204 | 2/2004 |
| JP | 2005-515309 | 5/2005 |
| JP | 2006-257000 | 9/2006 |
| JP | 2007-303015 | 11/2007 |
| JP | 2009-521921 | 6/2009 |
| JP | 2010-024586 | 2/2010 |
| JP | 4945768 B | 6/2012 |
| JP | 2012-136795 | 7/2012 |
| JP | 5427322 B | 2/2014 |
| JP | 5584932 | 9/2014 |
| WO | 92/09695 | 6/1992 |
| WO | 2001/036531 | 5/2001 |
| WO | 01/53333 | 7/2001 |
| WO | 01/070973 | 9/2001 |
| WO | 2007/078239 | 7/2007 |
| WO | 2008/004356 | 1/2008 |
| WO | 2010/015419 | 2/2010 |
| WO | 2010/123450 | 10/2010 |
| WO | 2011/113592 | 9/2011 |
| WO | 2012/165477 | 12/2012 |
| WO | 2013/065650 | 5/2013 |
| WO | 2013/065651 | 5/2013 |
| WO | 2014/103846 | 7/2014 |

OTHER PUBLICATIONS

Sekiyama: "Artificial Synthesis of Dream Fiber "Spider Silk""; the Journal of the Japanese Society for Cutaneous Health, Aug. 2011, No. 66, pp. 1-10 with its partial English translation (13 pages).

Sugihara et al.: "Artificial Production of Spider Silk Fibers"; Polymer Preprints, Japan, 2011, vol. 60, No. 22, pp. 5338-5339 with its partial English translation (6 pages).

Teule et al.: "A protocol for the production of recombinant spider silk-like proteins for artificial fiber spinning"; Nature Protocols, 2009, vol. 4, No. 3, pp. 341-355.

Heim et al.: "Spider Silk: From Soluble Protein to Extraordinary Fiber", Angewandte. Chem. Int. Ed., 2009, vol. 48, No. 20, pp. 3584-3596.

Diao, et al., "Solubility and Electrospun Regenerated Fiber of Two Different Kinds of Spider Silk", Journal of Materials Science & Engineering, vol. 26, No. 6, Dec. 2008, pp. 918-922 with an English abstract.

Kearns, et al., "Silk-based Biomaterials for Tissue Engineering", Topics in Tissue Engineering, vol. 4, 2008, pp. 1-19.

Elices et al.: "Bioinspired Fibers Follow the Track of Natural Spider Silk"; Macromolecules (2011), 44, pp. 1166-1176.

Guerette et al.: "Silk Properties Determined by Gland-Specific Expression of a Spider Fibroin Gene Family"; Science (1996), vol. 727, pp. 112-115.

Xia et al.: "Native-sized recombinant spider silk protein produced in metabolically engineered Escherichia coli results in a strong fiber"; Proc. Natl. Acad. Sci. (PNAS) (2010), vol. 107, No. 32, pp. 14059-14063.

Agnarsson et al.: "Bioprospecting Finds the Toughest Biological Material: Extraordinary Silk from a Giant Riverine Orb Spider"; PLOS ONE, vol. 5, Issue 9, Sep. 2010.

Extended European Search Report, dated Feb. 9, 2015; European Application No. 12793074.1 (9 pages).

Office Action issued in corresponding Chinese Application No. 201380034158.4, dated Jul. 27, 2015, 7 pages.

Extended European Search Report issued in corresponding European Application No. 13810001.1, dated Dec. 18, 2015, 7 pages.

Office Action issued in corresponding Chinese Patent Application No. 201380034158.4, dated Feb. 29, 2016, 12 pages with a partial English translation.

Tsukada, et al., Structural Changes and Dyeability of Silk Fibroin Fiber Following Shrinkage in Neutral Salt Solution, J. Appl. Polymer Sci, 1994, 51(4), pp. 619-624.

Phipps, et al., "Analysis of Azo Dyes Using a Core Enhanced Technology Accucore HPLC Column", Thremo Scientific, Aug. 2011, pp. 1-2, Retrieved from <hpps://tools.thermofisher.com/content/sfs/brochures/ANCCSCENTAZODYE_0611.pdf >.

Lopez-Cortes, et al., "Screening and Isolation of PHB-Producing Bacteria in a Polluted Marine Microbial Mat", Microb Ecol (2008) 56:112-120, DOI 10.1007/s00248-007-9329-8.

Davies, et al., (2003) "Measurement of Isoketal Protein Adducts by Liquid Chromatography-electrospray Ionization/Tandem Mass Spectrometry", In Hensley & Ford (Eds.), Methods in Bioligial Oxidate Stress (Chapter 15, p. 30), Totowa, new Jersey:Humana Ptress.

Teramoto, et al., "Chemical Modification of Silk Sericin in Lithium Chloride/Dimethyl Sulfoxide Solvent with 4-Cyanophenyl Isocyanate Biomacromolecules", 2004, 5(4), pp. 1392-1398.

(56) References Cited

OTHER PUBLICATIONS

Desai, et al., "Assessing the Structural Integrity of a Lyophilized Protein in Organic Solvents", Journal of the American Chemical Society, 1995, 117(14), pp. 3940-3945.
Kiyoichi Matsumoto, et al., "Regenerated Protein Fibers. I. Research and Development of a Novel Solvent for Silk Fibroin", Journal of Polymer Science, Part A: Polymer Chemistry, vol. 35, No. 10, Jul. 30, 1997, pp. 1949-1954.
Sashina, et al., "Structure and Solubility of Natural Silk Fibroiin", Russian Journal of Applied Chemistry, vol. 79, No. 6, Jun. 1, 2006, pp. 869-876.
Hardy, et al., "Polymeric Materials based on silk proteins", Polymer, vol. 49, No. 20, Sep. 23, 2008, pp. 4309-4327.
Lazaris, et al., "Spider Silk Fibers Spun from Soluble Recombinant Silk Produced in Mammalian Cells", Science, vol. 295, No. 5554, Jan. 18, 2002, pp. 472-476.
Extended European Search report issued in European Application No. 16776502.3, dated Jul. 26, 2018, 12 pages.
Extended European Search report issued in European Application No. 16776503.1, dated Jul. 20, 2018, 8 pages.

* cited by examiner

SEQUENCE LISTING

```
<160> NUMBER OF SEQ ID NOS: 13

<210> SEQ ID NO 1
<211> LENGTH: 1154
<212> TYPE: PRT
<213> ORGANISM: Artificial
<220> FEATURE:
<223> OTHER INFORMATION: ADF3Kai-Large-NRSH1

<400> SEQUENCE: 1

Met His His His His His His His His His Ser Ser Gly Ser Ser
1               5                   10                  15
```

```
Leu Glu Val Leu Phe Gln Pro Ala Arg Ala Gly Ser Gly Gln Gln
         20                  25                  30

Gly Pro Gly Gln Gln Gly Pro Gln Gln Gly Pro Gln Gln Gly
         35                  40                  45

Pro Tyr Gly Pro Gly Ala Ser Ala Ala Ala Ala Ala Gly Gly Tyr
 50                  55                  60

Gly Pro Gly Ser Gly Gln Gln Gly Pro Ser Gln Gln Gly Pro Gly Gln
 65                  70                  75                  80

Gln Gly Pro Gly Gly Gln Gly Pro Tyr Gly Pro Gly Ala Ser Ala Ala
             85                  90                  95

Ala Ala Ala Ala Gly Gly Tyr Gly Pro Gly Ser Gly Gln Gly Pro
         100                 105                 110

Gly Gly Gln Gly Pro Tyr Gly Pro Gly Ser Ser Ala Ala Ala Ala
         115                 120                 125

Ala Gly Gly Asn Gly Pro Gly Ser Gly Gln Gln Gly Ala Gly Gln Gln
         130                 135                 140

Gly Pro Gly Gln Gln Gly Pro Gly Ala Ser Ala Ala Ala Ala Ala
145                 150                 155                 160

Gly Gly Tyr Gly Pro Gly Ser Gly Gln Gln Gly Pro Gly Gln Gln Gly
                 165                 170                 175

Pro Gly Gly Gln Gly Pro Tyr Gly Pro Gly Ala Ser Ala Ala Ala Ala
                 180                 185                 190

Ala Ala Gly Gly Tyr Gly Pro Gly Ser Gly Gln Gly Pro Gly Gln Gln
                 195                 200                 205

Gly Pro Gly Gly Gln Gly Pro Tyr Gly Pro Gly Ala Ser Ala Ala Ala
                 210                 215                 220

Ala Ala Ala Gly Gly Tyr Gly Pro Gly Ser Gln Gln Gly Pro Gly
225                 230                 235                 240

Gln Gln Gly Pro Gly Gln Gln Gly Pro Gly Gly Gln Gly Pro Tyr Gly
                 245                 250                 255

Pro Gly Ala Ser Ala Ala Ala Ala Ala Gly Gly Tyr Gly Pro Gly
                 260                 265                 270

Tyr Gly Gln Gln Gly Pro Gly Gln Gln Gly Pro Gly Gln Gln Gly Pro
                 275                 280                 285

Tyr Gly Pro Gly Ala Ser Ala Ala Ser Ala Ala Ser Gly Gly Tyr Gly
                 290                 295                 300

Pro Gly Ser Gly Gln Gln Gly Pro Gly Gln Gln Gly Pro Gly Gly Gln
305                 310                 315                 320

Gly Pro Tyr Gly Pro Gly Ala Ser Ala Ala Ala Ala Ala Gly Gly
                 325                 330                 335

Tyr Gly Pro Gly Ser Gly Gln Gln Gly Pro Gly Gln Gln Gly Pro Gly
                 340                 345                 350

Gln Gln Gly Pro Gly Gln Gln Gly Pro Gly Gly Gln Gly Pro Tyr Gly
                 355                 360                 365

Pro Gly Ala Ser Ala Ala Ala Ala Ala Ala Gly Gly Tyr Gly Pro Gly
                 370                 375                 380

Ser Gly Gln Gln Gly Pro Gly Gln Gln Gly Pro Gly Gln Gln Gly Pro
385                 390                 395                 400

Gly Gln Gln Gly Pro Gly Gln Gln Gly Pro Gly Gln Gln Gly Pro Gly
                 405                 410                 415

Gln Gln Gly Pro Gly Gln Gln Gly Pro Gly Gln Gln Gly Pro Gly Gly
                 420                 425                 430
```

```
Gln Gly Ala Tyr Gly Pro Gly Ser Ala Ala Ala Ala Gly
            435                 440                 445
Gly Tyr Gly Pro Gly Ser Gly Gln Gln Gly Pro Gly Gln Gln Gly Pro
450                 455                 460
Gly Gln Gln Gly Pro Gly Gln Gln Gly Pro Gly Gln Gln Gly Pro Gly
465                 470                 475                 480
Gln Gln Gly Pro Gly Gln Gln Gly Pro Gly Gln Gln Gly Pro Tyr Gly
                485                 490                 495
Pro Gly Ala Ser Ala Ala Ala Ala Ala Gly Gly Tyr Gly Pro Gly
            500                 505                 510
Ser Gly Gln Gln Gly Pro Gly Gln Gln Gly Pro Gly Gln Gln Gly Pro
            515                 520                 525
Gly Gly Gln Gly Pro Tyr Gly Pro Gly Ala Ala Ser Ala Ala Val Ser
530                 535                 540
Val Ser Arg Ala Arg Ala Gly Ser Gly Gln Gln Gly Pro Gly Gln Gln
545                 550                 555                 560
Gly Pro Gly Gln Gln Gly Pro Gly Gln Gln Gly Pro Tyr Gly Pro Gly
                565                 570                 575
Ala Ser Ala Ala Ala Ala Ala Ala Gly Gly Tyr Gly Pro Gly Ser Gly
            580                 585                 590
Gln Gln Gly Pro Ser Gln Gly Pro Gly Gln Gln Gly Pro Gly Gly
            595                 600                 605
Gln Gly Pro Tyr Gly Pro Gly Ala Ser Ala Ala Ala Ala Ala Ala Gly
            610                 615                 620
Gly Tyr Gly Pro Gly Ser Gly Gln Gln Gly Pro Gly Gly Gln Gly Pro
625                 630                 635                 640
Tyr Gly Pro Gly Ser Ser Ala Ala Ala Ala Ala Gly Gly Asn Gly
                645                 650                 655
Pro Gly Ser Gly Gln Gln Gly Ala Gly Gln Gln Gly Pro Gly Gln Gln
                660                 665                 670
Gly Pro Gly Ala Ser Ala Ala Ala Ala Ala Gly Gly Tyr Gly Pro
            675                 680                 685
Gly Ser Gly Gln Gln Gly Pro Gly Gln Gln Gly Pro Gly Gly Gln Gly
            690                 695                 700
Pro Tyr Gly Pro Gly Ala Ser Ala Ala Ala Ala Ala Ala Gly Gly Tyr
705                 710                 715                 720
Gly Pro Gly Ser Gly Gln Gly Pro Gly Gln Gln Gly Pro Gly Gln
                725                 730                 735
Gly Pro Tyr Gly Pro Gly Ala Ser Ala Ala Ala Ala Ala Ala Gly Gly
            740                 745                 750
Tyr Gly Pro Gly Ser Gly Gln Gln Gly Pro Gly Gln Gln Gly Pro Gly
            755                 760                 765
Gln Gln Gly Pro Gly Gly Gln Gly Pro Tyr Gly Pro Gly Ala Ser Ala
            770                 775                 780
Ala Ala Ala Ala Gly Gly Tyr Gly Pro Gly Tyr Gly Gln Gln Gly
785                 790                 795                 800
Pro Gly Gln Gln Gly Pro Gly Gly Gln Gly Pro Tyr Gly Pro Gly Ala
                805                 810                 815
Ser Ala Ala Ser Ala Ala Ser Gly Gly Tyr Gly Pro Gly Ser Gly Gln
            820                 825                 830
Gln Gly Pro Gly Gln Gln Gly Pro Gly Gly Gln Gly Pro Tyr Gly Pro
            835                 840                 845
```

-continued

Gly Ala Ser Ala Ala Ala Ala Ala Gly Gly Tyr Gly Pro Gly Ser
        850                 855                 860

Gly Gln Gln Gly Pro Gly Gln Gln Gly Pro Gly Gln Gln Gly Pro Gly
865                 870                 875                 880

Gln Gln Gly Pro Gly Gln Gln Gly Pro Tyr Gly Pro Gly Ala Ser Ala
                885                 890                 895

Ala Ala Ala Ala Ala Gly Gly Tyr Gly Pro Gly Ser Gly Gln Gln Gly
            900                 905                 910

Pro Gly Gln Gln Gly Pro Gly Gln Gln Gly Pro Gly Gln Gln Gly Pro
        915                 920                 925

Gly Gln Gln Gly Pro Gly Gln Gln Gly Pro Gly Gln Gln Gly Pro Gly
    930                 935                 940

Gln Gln Gly Pro Gly Gln Gln Gly Pro Gly Gln Gly Ala Tyr Gly
945                 950                 955                 960

Pro Gly Ala Ser Ala Ala Gly Ala Ala Gly Gly Tyr Gly Pro Gly
                965                 970                 975

Ser Gly Gln Gln Gly Pro Gly Gln Gln Gly Pro Gly Gln Gln Gly Pro
            980                 985                 990

Gly Gln Gln Gly Pro Gly Gln Gln Gly Pro Gly Gln Gln Gly Pro Gly
        995                 1000                1005

Gln Gln Gly Pro Gly Gln Gln Gly Pro Tyr Gly Pro Gly Ala Ser
        1010                1015                1020

Ala Ala Ala Ala Ala Ala Gly Gly Tyr Gly Pro Gly Ser Gly Gln
        1025                1030                1035

Gln Gly Pro Gly Gln Gln Gly Pro Gly Gln Gln Gly Pro Gly Gly
        1040                1045                1050

Gln Gly Pro Tyr Gly Pro Gly Ala Ala Ser Ala Ala Val Ser Val
        1055                1060                1065

Gly Gly Tyr Gly Pro Gln Ser Ser Ser Val Pro Val Ala Ser Ala
        1070                1075                1080

Val Ala Ser Arg Leu Ser Ser Pro Ala Ala Ser Ser Arg Val Ser
        1085                1090                1095

Ser Ala Val Ser Ser Leu Val Ser Ser Gly Pro Thr Lys His Ala
        1100                1105                1110

Ala Leu Ser Asn Thr Ile Ser Ser Val Val Ser Gln Val Ser Ala
        1115                1120                1125

Ser Asn Pro Gly Leu Ser Gly Cys Asp Val Leu Val Gln Ala Leu
        1130                1135                1140

Leu Glu Val Val Ser Ala Leu Val Ser Ile Leu
        1145                1150

<210> SEQ ID NO 2
<211> LENGTH: 660
<212> TYPE: PRT
<213> ORGANISM: Artificial
<220> FEATURE:
<223> OTHER INFORMATION: ADF3Kai

<400> SEQUENCE: 2

Met His His His His His His His His Ser Ser Gly Ser Ser
1               5                   10                  15

Leu Glu Val Leu Phe Gln Gly Pro Ala Arg Ala Gly Ser Gly Gln Gln
            20                  25                  30

Gly Pro Gly Gln Gln Gly Pro Gly Gln Gln Gly Pro Gly Gln Gln Gly
        35                  40                  45

Pro Tyr Gly Pro Gly Ala Ser Ala Ala Ala Ala Ala Gly Gly Tyr
        50                  55                  60

Gly Pro Gly Ser Gly Gln Gln Gly Pro Ser Gln Gln Gly Pro Gly Gln
65                  70                  75                  80

Gln Gly Pro Gly Gln Gly Pro Tyr Gly Pro Gly Ala Ser Ala Ala
                85                  90                  95

Ala Ala Ala Ala Gly Gly Tyr Gly Pro Gly Ser Gly Gln Gln Gly Pro
            100                 105                 110

Gly Gly Gln Gly Pro Tyr Gly Pro Gly Ser Ser Ala Ala Ala Ala
            115                 120                 125

Ala Gly Gly Asn Gly Pro Gly Ser Gly Gln Gln Gly Ala Gly Gln Gln
            130                 135                 140

Gly Pro Gly Gln Gln Gly Pro Gly Ala Ser Ala Ala Ala Ala Ala
145                 150                 155                 160

Gly Gly Tyr Gly Pro Gly Ser Gly Gln Gln Gly Pro Gly Gln Gln Gly
                165                 170                 175

Pro Gly Gly Gln Gly Pro Tyr Gly Pro Gly Ala Ser Ala Ala Ala Ala
            180                 185                 190

Ala Ala Gly Gly Tyr Gly Pro Gly Ser Gly Gln Gly Pro Gly Gln Gln
            195                 200                 205

Gly Pro Gly Gly Gln Gly Pro Tyr Gly Pro Gly Ala Ser Ala Ala Ala
210                 215                 220

Ala Ala Ala Gly Gly Tyr Gly Pro Gly Ser Gly Gln Gln Gly Pro Gly
225                 230                 235                 240

Gln Gln Gly Pro Gly Gln Gln Gly Pro Gly Gln Gly Pro Tyr Gly
                245                 250                 255

Pro Gly Ala Ser Ala Ala Ala Ala Ala Gly Gly Tyr Gly Pro Gly
            260                 265                 270

Tyr Gly Gln Gln Gly Pro Gly Gln Gln Gly Pro Gly Gln Gly Pro
            275                 280                 285

Tyr Gly Pro Gly Ala Ser Ala Ala Ser Ala Ala Ser Gly Gly Tyr Gly
            290                 295                 300

Pro Gly Ser Gly Gln Gln Gly Pro Gly Gln Gln Gly Pro Gly Gly Gln
305                 310                 315                 320

Gly Pro Tyr Gly Pro Gly Ala Ser Ala Ala Ala Ala Ala Gly Gly
                325                 330                 335

Tyr Gly Pro Gly Ser Gly Gln Gln Gly Pro Gly Gln Gln Gly Pro Gly
            340                 345                 350

Gln Gln Gly Pro Gly Gln Gln Gly Pro Gly Gln Gly Pro Tyr Gly
            355                 360                 365

Pro Gly Ala Ser Ala Ala Ala Ala Ala Gly Gly Tyr Gly Pro Gly
            370                 375                 380

Ser Gly Gln Gln Gly Pro Gly Gln Gln Gly Pro Gly Gln Gln Gly Pro
385                 390                 395                 400

Gly Gln Gln Gly Pro Gly Gln Gln Gly Pro Gly Gln Gln Gly Pro Gly
                405                 410                 415

Gln Gln Gly Pro Gly Gln Gln Gly Pro Gly Gln Gln Gly Pro Gly Gly
            420                 425                 430

Gln Gly Ala Tyr Gly Pro Gly Ala Ser Ala Ala Gly Ala Ala Gly
            435                 440                 445

Gly Tyr Gly Pro Gly Ser Gly Gln Gln Gly Pro Gly Gln Gln Gly Pro
450                 455                 460

```
Gly Gln Gln Gly Pro Gly Gln Gln Gly Pro Gly Gln Gln Gly Pro Gly
465                 470                 475                 480

Gln Gln Gly Pro Gly Gln Gln Gly Pro Gly Gln Gln Gly Pro Tyr Gly
            485                 490                 495

Pro Gly Ala Ser Ala Ala Ala Ala Ala Gly Gly Tyr Gly Pro Gly
        500                 505                 510

Ser Gly Gln Gln Gly Pro Gly Gln Gln Gly Pro Gly Gln Gln Gly Pro
        515                 520                 525

Gly Gln Gln Gly Pro Tyr Gly Pro Gly Ala Ala Ser Ala Ala Val Ser
        530                 535                 540

Val Gly Gly Tyr Gly Pro Gln Ser Ser Val Pro Val Ala Ser Ala
545                 550                 555                 560

Val Ala Ser Arg Leu Ser Ser Pro Ala Ala Ser Ser Arg Val Ser Ser
                565                 570                 575

Ala Val Ser Ser Leu Val Ser Ser Gly Pro Thr Lys His Ala Ala Leu
                580                 585                 590

Ser Asn Thr Ile Ser Ser Val Val Ser Gln Val Ser Ala Ser Asn Pro
        595                 600                 605

Gly Leu Ser Gly Cys Asp Val Leu Val Gln Ala Leu Leu Glu Val Val
        610                 615                 620

Ser Ala Leu Val Ser Ile Leu Gly Ser Ser Ile Gly Gln Ile Asn
625                 630                 635                 640

Tyr Gly Ala Ser Ala Gln Tyr Thr Gln Met Val Gly Ser Val Ala
                645                 650                 655

Gln Ala Leu Ala
        660

<210> SEQ ID NO 3
<211> LENGTH: 1183
<212> TYPE: PRT
<213> ORGANISM: Artificial
<220> FEATURE:
<223> OTHER INFORMATION: ADF3Kai-Large

<400> SEQUENCE: 3

Met His His His His His His His His Ser Ser Gly Ser Ser
1               5                   10                  15

Leu Glu Val Leu Phe Gln Gly Pro Ala Arg Ala Gly Ser Gly Gln Gln
            20                  25                  30

Gly Pro Gly Gln Gln Gly Pro Gly Gln Gln Gly Pro Gly Gln Gln Gly
            35                  40                  45

Pro Tyr Gly Pro Gly Ala Ser Ala Ala Ala Ala Ala Gly Gly Tyr
    50                  55                  60

Gly Pro Gly Ser Gly Gln Gln Gly Pro Ser Gln Gln Gly Pro Gly Gln
65                  70                  75                  80

Gln Gly Pro Gly Gly Gln Gly Pro Tyr Gly Pro Gly Ala Ser Ala Ala
            85                  90                  95

Ala Ala Ala Ala Gly Gly Tyr Gly Pro Gly Ser Gly Gln Gln Gly Pro
            100                 105                 110

Gly Gly Gln Gly Pro Tyr Gly Pro Gly Ser Ser Ala Ala Ala Ala
            115                 120                 125

Ala Gly Gly Asn Gly Pro Gly Ser Gly Gln Gln Gly Ala Gly Gln Gln
            130                 135                 140

Gly Pro Gly Gln Gln Gly Pro Gly Ala Ser Ala Ala Ala Ala Ala
145                 150                 155                 160
```

-continued

```
Gly Gly Tyr Gly Pro Gly Ser Gly Gln Gln Gly Pro Gly Gln Gln Gly
                165                 170                 175
Pro Gly Gly Gln Gly Pro Tyr Gly Pro Gly Ala Ser Ala Ala Ala Ala
            180                 185                 190
Ala Ala Gly Gly Tyr Gly Pro Gly Ser Gly Gln Gln Gly Pro Gly Gln Gln
        195                 200                 205
Gly Pro Gly Gly Gln Gly Pro Tyr Gly Pro Gly Ala Ser Ala Ala Ala
    210                 215                 220
Ala Ala Ala Gly Gly Tyr Gly Pro Gly Ser Gly Gln Gln Gly Pro Gly
225                 230                 235                 240
Gln Gln Gly Pro Gly Gln Gln Gly Pro Gly Gln Gly Pro Tyr Gly
                245                 250                 255
Pro Gly Ala Ser Ala Ala Ala Ala Ala Gly Gly Tyr Gly Pro Gly
            260                 265                 270
Tyr Gly Gln Gln Gly Pro Gly Gln Gln Gly Pro Gly Gln Gly Pro
        275                 280                 285
Tyr Gly Pro Gly Ala Ser Ala Ser Ala Ala Ser Gly Gly Tyr Gly
        290                 295                 300
Pro Gly Ser Gly Gln Gln Gly Pro Gly Gln Gln Gly Pro Gly Gln
305                 310                 315                 320
Gly Pro Tyr Gly Pro Gly Ala Ser Ala Ala Ala Ala Ala Gly Gly
                325                 330                 335
Tyr Gly Pro Gly Ser Gly Gln Gln Gly Pro Gly Gln Gln Gly Pro Gly
                340                 345                 350
Gln Gln Gly Pro Gly Gln Gln Gly Pro Gly Gln Gly Pro Tyr Gly
                355                 360                 365
Pro Gly Ala Ser Ala Ala Ala Ala Ala Gly Gly Tyr Gly Pro Gly
            370                 375                 380
Ser Gly Gln Gln Gly Pro Gly Gln Gln Gly Pro Gly Gln Gln Gly Pro
385                 390                 395                 400
Gly Gln Gln Gly Pro Gly Gln Gln Gly Pro Gly Gln Gln Gly Pro Gly
                405                 410                 415
Gln Gln Gly Pro Gly Gln Gln Gly Pro Gly Gln Gln Gly Pro Gly Gly
                420                 425                 430
Gln Gly Ala Tyr Gly Pro Gly Ala Ser Ala Ala Ala Gly Ala Ala Gly
            435                 440                 445
Gly Tyr Gly Pro Gly Ser Gly Gln Gln Gly Pro Gly Gln Gln Gly Pro
        450                 455                 460
Gly Gln Gln Gly Pro Gly Gln Gln Gly Pro Gly Gln Gln Gly Pro Gly
465                 470                 475                 480
Gln Gln Gly Pro Gly Gln Gln Gly Pro Gly Gln Gln Gly Pro Tyr Gly
                485                 490                 495
Pro Gly Ala Ser Ala Ala Ala Ala Ala Gly Gly Tyr Gly Pro Gly
            500                 505                 510
Ser Gly Gln Gln Gly Pro Gly Gln Gln Gly Pro Gly Gln Gln Gly Pro
        515                 520                 525
Gly Gly Gln Gly Pro Tyr Gly Pro Gly Ala Ala Ser Ala Ala Val Ser
        530                 535                 540
Val Ser Arg Ala Arg Ala Gly Ser Gly Gln Gln Gly Pro Gly Gln Gln
545                 550                 555                 560
Gly Pro Gly Gln Gln Gly Pro Gly Gln Gln Gly Pro Tyr Gly Pro Gly
                565                 570                 575
```

-continued

```
Ala Ser Ala Ala Ala Ala Ala Gly Gly Tyr Pro Gly Ser Gly
            580                 585                 590

Gln Gln Gly Pro Ser Gln Gly Pro Gly Gln Gly Pro Gly Gly
        595                 600                 605

Gln Gly Pro Tyr Gly Pro Gly Ala Ser Ala Ala Ala Ala Gly
    610                 615                 620

Gly Tyr Gly Pro Gly Ser Gly Gln Gln Gly Pro Gly Gln Gly Pro
625                 630                 635                 640

Tyr Gly Pro Gly Ser Ser Ala Ala Ala Ala Gly Gly Asn Gly
                645                 650                 655

Pro Gly Ser Gly Gln Gln Gly Ala Gly Gln Gly Pro Gly Gln Gln
            660                 665                 670

Gly Pro Gly Ala Ser Ala Ala Ala Ala Gly Gly Tyr Gly Pro
        675                 680                 685

Gly Ser Gly Gln Gln Gly Pro Gly Gln Gln Gly Pro Gly Gln Gly
    690                 695                 700

Pro Tyr Gly Pro Gly Ala Ser Ala Ala Ala Ala Gly Gly Tyr
705                 710                 715                 720

Gly Pro Gly Ser Gly Gln Gly Pro Gly Gln Gln Gly Pro Gly Gln
                725                 730                 735

Gly Pro Tyr Gly Pro Gly Ala Ser Ala Ala Ala Ala Gly Gly
            740                 745                 750

Tyr Gly Pro Gly Ser Gly Gln Gln Gly Pro Gly Gln Gln Gly Pro Gly
        755                 760                 765

Gln Gln Gly Pro Gly Gly Gln Gly Pro Tyr Gly Pro Gly Ala Ser Ala
    770                 775                 780

Ala Ala Ala Ala Gly Gly Tyr Gly Pro Gly Tyr Gly Gln Gln Gly
785                 790                 795                 800

Pro Gly Gln Gln Gly Pro Gly Gln Gly Pro Tyr Gly Pro Gly Ala
                805                 810                 815

Ser Ala Ala Ser Ala Ala Ser Gly Gly Tyr Gly Pro Gly Ser Gly Gln
            820                 825                 830

Gln Gly Pro Gly Gln Gln Gly Pro Gly Gln Gly Pro Tyr Gly Pro
        835                 840                 845

Gly Ala Ser Ala Ala Ala Ala Ala Gly Gly Tyr Gly Pro Gly Ser
    850                 855                 860

Gly Gln Gln Gly Pro Gly Gln Gln Gly Pro Gly Gln Gln Gly Pro Gly
865                 870                 875                 880

Gln Gln Gly Pro Gly Gln Gly Pro Tyr Gly Pro Gly Ala Ser Ala
                885                 890                 895

Ala Ala Ala Ala Gly Gly Tyr Gly Pro Gly Ser Gly Gln Gln Gly
            900                 905                 910

Pro Gly Gln Gln Gly Pro Gly Gln Gln Gly Pro Gly Gln Gln Gly Pro
        915                 920                 925

Gly Gln Gln Gly Pro Gly Gln Gln Gly Pro Gly Gln Gln Gly Pro Gly
    930                 935                 940

Gln Gln Gly Pro Gly Gln Gln Gly Pro Gly Gln Gly Ala Tyr Gly
945                 950                 955                 960

Pro Gly Ala Ser Ala Ala Ala Gly Ala Ala Gly Gly Tyr Gly Pro Gly
                965                 970                 975

Ser Gly Gln Gln Gly Pro Gly Gln Gln Gly Pro Gly Gln Gln Gly Pro
            980                 985                 990
```

Gly Gln Gln Gly Pro Gly Gln Gln Gly Pro Gly Gln Gln Gly Pro Gly
            995                 1000                1005

Gln Gln Gly Pro Gly Gln Gln Gly Pro Tyr Gly Pro Gly Ala Ser
    1010                1015                1020

Ala Ala Ala Ala Ala Ala Gly Gly Tyr Gly Pro Gly Ser Gly Gln
    1025                1030                1035

Gln Gly Pro Gly Gln Gln Gly Pro Gly Gln Gln Gly Pro Gly Gly
    1040                1045                1050

Gln Gly Pro Tyr Gly Pro Gly Ala Ala Ser Ala Ala Val Ser Val
    1055                1060                1065

Gly Gly Tyr Gly Pro Gln Ser Ser Ser Val Pro Val Ala Ser Ala
    1070                1075                1080

Val Ala Ser Arg Leu Ser Ser Pro Ala Ala Ser Ser Arg Val Ser
    1085                1090                1095

Ser Ala Val Ser Ser Leu Val Ser Ser Gly Pro Thr Lys His Ala
    1100                1105                1110

Ala Leu Ser Asn Thr Ile Ser Ser Val Val Ser Gln Val Ser Ala
    1115                1120                1125

Ser Asn Pro Gly Leu Ser Gly Cys Asp Val Leu Val Gln Ala Leu
    1130                1135                1140

Leu Glu Val Val Ser Ala Leu Val Ser Ile Leu Gly Ser Ser Ser
    1145                1150                1155

Ile Gly Gln Ile Asn Tyr Gly Ala Ser Ala Gln Tyr Thr Gln Met
    1160                1165                1170

Val Gly Gln Ser Val Ala Gln Ala Leu Ala
    1175                1180

<210> SEQ ID NO 4
<211> LENGTH: 24
<212> TYPE: PRT
<213> ORGANISM: Artificial
<220> FEATURE:
<223> OTHER INFORMATION: His tag and start codon

<400> SEQUENCE: 4

Met His His His His His His His His His Ser Ser Gly Ser Ser
1               5                   10                  15

Leu Glu Val Leu Phe Gln Gly Pro
            20

<210> SEQ ID NO 5
<211> LENGTH: 1983
<212> TYPE: DNA
<213> ORGANISM: Artificial
<220> FEATURE:
<223> OTHER INFORMATION: ADF3Kai

<400> SEQUENCE: 5
atgcatcacc atcatcatca tcaccaccac cattcctcgg gctcatcctt ggaagtgtta      60
tttcaaggac cagcacgagc cggttcggga caacaagggc ctggccagca gggcccaggt     120
caacaagggc caggacagca gggtccttat gggcccggcg caagcgcagc agctgcggcc     180
gctggtggct atggtcctgg ctccggtcaa cagggccctt cgcaacaagg tcccgggcag     240
caaggtcctg gtggccaggg tcccctacgg gccggggcga gtgcggcagc agccgctgca     300
ggcggttatg gtccaggaag cggacagcaa ggtccgggag gtcaaggtcc gtatggccca     360
ggctctagcg cggctgccgc tgccgcgggt ggcaacggac agggagcgg acaacagggc      420

| | |
|---|---|
| gcgggacaac agggtccagg acagcaaggc ccagggcgt cggcggctgc agcggcggcc | 480 |
| ggaggctatg acccggctc aggacaacag ggaccgggtc aacaaggacc cgtggccaa | 540 |
| ggccctatg gcccgggcgc cagcgcggcc gcagccgccg cgggcgggta cggccccggt | 600 |
| agcggccagg gaccaggtca gcaggggcca ggaggtcagg gcccatacgg tccgggcgca | 660 |
| tccgcggcgg cggcagcggc aggtggctac ggtcccggaa gcggccaaca ggggccaggg | 720 |
| caacaaggac caggacaaca aggtcctggg ggccaaggac cgtatggacc aggagcatca | 780 |
| gctgcagccg cggcagctgg cggttacggt ccaggctacg gccagcaggg tccgggtcag | 840 |
| cagggaccgg gaggccaggg gccttatggc cctggcgctt ccgcagccag tgccgcttct | 900 |
| ggaggatacg ggccgggaag cggtcagcaa ggccctggcc aacaaggacc tggaggccaa | 960 |
| gggccctacg gcccaggagc ctcggcagcc gcagctgccg caggtgggta tgggccaggt | 1020 |
| agcgggcaac aagggccggg tcagcaagga ccggggcaac agggacctgg gcagcaagga | 1080 |
| cccggggtc aaggcccgta cggacctggt gcgtctgcag ctgctgctgc ggctggtgga | 1140 |
| tatggtccgg gatcggggca gcagggtccc ggtcagcagg gcctggtca gcaagggcca | 1200 |
| ggccaacagg gacccggaca acaaggcccg ggtcaacagg gtcctggaca gcaggggccg | 1260 |
| ggccaacaag gccctgggca cagggtccg ggggacagg gggcctatgg gcctggcgca | 1320 |
| tctgccgccg ctggcgcagc cggtgggtac gggcctgggt caggtcaaca ggggcctggt | 1380 |
| caacaaggcc ccgggcaaca gggccccggc cagcaaggtc cagggcagca gggccccgga | 1440 |
| cagcaagggc ctggacaaca ggggcccgga cagcagggac cttacgggcc cggtgcgagc | 1500 |
| gcagcggccg ccgccgcagg gggatatggc cccggatcgg ccagcaggg accaggccag | 1560 |
| caaggacctg gccaacaggg cccgggggt caggggccgt atggtcccgg cgctgcaagt | 1620 |
| gctgcagtgt ccgttggagg ttacggcccct cagtcttcgt ctgttccggt ggcgtccgca | 1680 |
| gttgcgagta gactgtcttc acctgctgct tcatcgcgag tatcgagcgc tgtttcgtct | 1740 |
| cttgtctcgt cgggtcccac gaaacatgcc gcctttcaa atacgatttc atctgtagtg | 1800 |
| tcccaagtta gtgcaagtaa cccgggggta tccggatgcg acgttctcgt tcaggcactc | 1860 |
| ctagaagtag tatccgcgtt ggtgagcatc ttaggcagct cctcgatagg tcaaataaac | 1920 |
| tatggtgctt cagcccagta tacacagatg gtgggacaga gcgtcgcgca ggcattggct | 1980 |
| taa | 1983 |

```
<210> SEQ ID NO 6
<211> LENGTH: 3552
<212> TYPE: DNA
<213> ORGANISM: Artificial
<220> FEATURE:
<223> OTHER INFORMATION: ADF3Kai-Large

<400> SEQUENCE: 6
```

| | |
|---|---|
| atgcatcacc atcatcatca tcaccaccac cattcctcgg gctcatcctt ggaagtgtta | 60 |
| tttcaaggac cagcacgagc cggttcggga caacaagggc ctggccagca gggcccaggt | 120 |
| caacaagggc caggacagca gggtccttat gggcccggcg caagcgcagc agctgcggcc | 180 |
| gctggtggct atggtcctgg ctccggtcaa cagggcccctt cgcaacaagg tcccgggcag | 240 |
| caaggtcctg gtgccaggg tccctacggg ccgggggcga gtgcggcagc agccgctgca | 300 |
| ggcggttatg gtccaggaag cggacagcaa ggtccgggag gtcaaggtcc gtatggccca | 360 |
| ggctctagcg cggctgccgc tgccgcgggt ggcaacggac cagggagcgg acaacagggc | 420 |
| gcgggacaac agggtccagg acagcaaggc ccagggcgt cggcggctgc agcggcggcc | 480 |

| | |
|---|---|
| ggaggctatg acccggctc aggacaacag ggaccgggtc aacaaggacc cgtggccaa | 540 |
| ggcccctatg gcccgggcgc cagcgcggcc gcagccgccg cgggcgggta cggcccggt | 600 |
| agcggccagg gaccaggtca gcaggggcca ggaggtcagg gcccatacgg tccgggcgca | 660 |
| tccgcggcgg cggcagcggc aggtggctac ggtcccggaa gcggccaaca ggggccaggg | 720 |
| caacaaggac caggacaaca aggtcctggg ggccaaggac cgtatggacc aggagcatca | 780 |
| gctgcagccg cggcagctgg cggttacggt ccaggctacg gccagcaggg tccgggtcag | 840 |
| cagggaccgg gaggccaggg gccttatggc cctggcgctt ccgcagccag tgccgcttct | 900 |
| ggaggatacg ggccgggaag cggtcagcaa ggccctggcc aacaaggacc tggaggccaa | 960 |
| gggccctacg gcccaggagc ctcggcagcc gcagctgccg caggtgggta tgggccaggt | 1020 |
| agcgggcaac aagggccggg tcagcaagga ccggggcaac agggacctgg gcagcaagga | 1080 |
| cccgggggtc aaggcccgta cggacctggt gcgtctgcag ctgctgctgc ggctggtgga | 1140 |
| tatggtccgg gatcggggca gcagggtccc ggtcagcagg gcctggtca gcaagggcca | 1200 |
| ggccaacagg gacccggaca caaggcccg ggtcaacagg gtcctggaca gcaggggccg | 1260 |
| ggccaacaag gccctgggca cagggtccg ggggacagg gggcctatgg gcctggcgca | 1320 |
| tctgccgccg ctggcgcagc cggtgggtac gggcctgggt caggtcaaca ggggcctggt | 1380 |
| caacaaggcc ccgggcaaca gggccccggc cagcaaggtc cagggcagca gggcccggga | 1440 |
| cagcaagggc ctgacaaca ggggcccgga cagcaggac cttacgggcc cggtgcgagc | 1500 |
| gcagcggccg ccgccgcagg gggatatggc cccggatcgg ccagcaggg accaggccag | 1560 |
| caaggacctg gccaacaggg cccgggggt cagggccgt atggtcccgg cgctgcaagt | 1620 |
| gctgcagtgt ccgtttctag agcacgagcc ggttcgggac aacaagggcc tggccagcag | 1680 |
| ggcccaggtc aacaagggcc aggacagcag ggtccttatg ggcccggcgc aagcgcagca | 1740 |
| gctgcggccg ctggtggcta tggtcctggc tccggtcaac agggcccttc gcaacaaggt | 1800 |
| cccgggcagc aaggtcctgg tggccaggt ccctacgggc cgggggcgag tgcggcagca | 1860 |
| gccgctgcag gcggttatgg tccaggaagc ggacagcaag gtccgggagg tcaaggtccg | 1920 |
| tatggcccag gctctagcgc ggctgccgct ccgcgggtg caacggacc agggagcgga | 1980 |
| caacagggcg cgggacaaca gggtccagga cagcaaggcc caggggcgtc ggcggctgca | 2040 |
| gcggcggccg gaggctatgg acccggctca ggacaacagg gaccgggtca acaaggaccc | 2100 |
| ggtggccaag gcccctatgg cccgggcgcc agcgcggccg cagccgccgc gggcgggtac | 2160 |
| ggcccccggta gcgccagggg accaggtcag caggggccag gaggtcaggg cccatacggt | 2220 |
| ccgggcgcat ccgcggcggc ggcagcggca ggtggctacg gtcccggaag cggccaacag | 2280 |
| gggccagggc aacaaggacc aggacaacaa ggtcctgggg gccaaggacc gtatggacca | 2340 |
| ggagcatcag ctgcagccgc ggcagctggc ggttacggtc caggctacgg ccagcagggt | 2400 |
| ccgggtcagc agggaccggg aggccagggg ccttatggcc ctggcgcttc cgcagccagt | 2460 |
| gccgcttctg gaggatacgg gccgggaagc ggtcagcaag gccctggcca acaaggacct | 2520 |
| ggaggccaag ggccctacgg cccaggagcc tcggcagccg cagctgccgc aggtgggtat | 2580 |
| gggccaggta gcgggcaaca agggccgggt cagcaaggac cggggcaaca gggacctggg | 2640 |
| cagcaaggac ccgggggtca aggcccgtac ggacctggtg cgtctgcagc tgctgctgcg | 2700 |
| gctggtggat atggtccggg atcggggcag cagggtcccg gtcagcaggg cctggtcag | 2760 |
| caagggccag gccaacaggg acccggacaa caaggcccgg gtcaacaggg tcctggacag | 2820 |

| | |
|---|---:|
| caggggccgg gccaacaagg ccctgggcaa cagggtccgg ggggacaggg ggcctatggg | 2880 |
| cctggcgcat ctgccgccgc tggcgcagcc ggtgggtacg ggcctgggtc aggtcaacag | 2940 |
| gggcctggtc aacaaggccc cggcaacag gccccggcc agcaaggtcc agggcagcag | 3000 |
| ggcccgggac agcaagggcc tggacaacag ggccccggac agcagggacc ttacgggccc | 3060 |
| ggtgcgagcg cagcggccgc cgccgcaggg ggatatggcc ccggatcggg ccagcaggga | 3120 |
| ccaggccagc aaggacctgg ccaacagggc ccggggggtc aggggccgta tggtcccggc | 3180 |
| gctgcaagtg ctgcagtgtc cgttggaggt tacggccctc agtcttcgtc tgttccggtg | 3240 |
| gcgtccgcag ttgcgagtag actgtcttca cctgctgctt catcgcgagt atcgagcgct | 3300 |
| gtttcgtctc ttgtctcgtc gggtcccacg aaacatgccg ccctttcaaa tacgatttca | 3360 |
| tctgtagtgt cccaagttag tgcaagtaac ccggggttat ccggatgcga cgttctcgtt | 3420 |
| caggcactcc tagaagtagt atccgcgttg gtgagcatct taggcagctc ctcgataggt | 3480 |
| caaataaact atggtgcttc agcccagtat acacagatgg tgggacagag cgtcgcgcag | 3540 |
| gcattggctt aa | 3552 |

<210> SEQ ID NO 7
<211> LENGTH: 3465
<212> TYPE: DNA
<213> ORGANISM: Artificial
<220> FEATURE:
<223> OTHER INFORMATION: ADF3Kai-Large-NRSH1

<400> SEQUENCE: 7

| | |
|---|---:|
| atgcatcacc atcatcatca tcaccaccac cattcctcgg gctcatcctt ggaagtgtta | 60 |
| tttcaaggac cagcacgagc cggttcggga caacaagggc ctggccagca gggcccaggt | 120 |
| caacaagggc caggacagca gggtccttat gggcccggcg caagcgcagc agctgcggcc | 180 |
| gctggtggct atggtcctgg ctccggtcaa cagggccctt cgcaacaagg tcccgggcag | 240 |
| caaggtcctg gtgccaggg tccctacggg cggggcga gtgcggcagc agccgctgca | 300 |
| ggcggttatg gtccaggaag cggacagcaa ggtccgggag gtcaaggtcc gtatggccca | 360 |
| ggctctagcg cggctgccgc tgccgcgggt ggcaacggac cagggagcgg acaacagggc | 420 |
| gcgggacaac agggtccagg acagcaaggc ccaggggcgt cggcggctgc agcggcggcc | 480 |
| ggaggctatg acccggctc aggacaacag ggaccgggtc aacaaggacc cggtggccaa | 540 |
| ggcccctatg gccgggcgc agcgcggcc gcagccgccg cgggcgggta cggccccggt | 600 |
| agcggccagg gaccaggtca gcaggggcca ggaggtcagg gcccatacgg tccgggcgca | 660 |
| tccgcggcgg cggcagcggc aggtggctac ggtcccggaa gcggccaaca ggggccaggg | 720 |
| caacaaggac caggacaaca aggtcctggg ggccaaggac cgtatggacc aggagcatca | 780 |
| gctgcagccg cggcagctgg cggttacggt ccaggctacg gccagcaggg tccgggtcag | 840 |
| cagggaccgg gaggccaggg gccttatggc cctggcgctt ccgcagccag tgccgcttct | 900 |
| ggaggatacg ggcgggaag cggtcagcaa ggccctggcc aacaaggacc tggaggccaa | 960 |
| gggccctacg gccaggagc ctcggcagcc gcagctgccg caggtgggta tgggccaggt | 1020 |
| agcgggcaac aagggccggg tcagcaagga ccggggcaac agggacctgg cagcaagga | 1080 |
| cccgggggtc aaggcccgta cggacctggt gcgtctgcag ctgctgctgc ggctggtgga | 1140 |
| tatggtccgg gatcggggca gcagggtccc ggtcagcagg gcctggtca gcaagggcca | 1200 |
| ggccaacagg gacccggaca acaaggcccg ggtcaacagg gtcctggaca gcaggggccg | 1260 |
| ggccaacaag gccctgggca acagggtccg ggggacagg gggcctatgg gcctggcgca | 1320 |

```
tctgccgccg ctggcgcagc cggtgggtac gggcctgggt caggtcaaca ggggcctggt    1380
caacaaggcc ccgggcaaca gggccccggc cagcaaggtc cagggcagca gggcccggga    1440
cagcaagggc ctggacaaca ggggcccgga cagcagggac cttacgggcc cggtgcgagc    1500
gcagcggccg ccgccgcagg gggatatggc cccggatcgg ccagcaggg accaggccag    1560 caaggacctg gccaacaggg cccgggggt caggggccgt atggtcccgg cgctgcaagt    1620
gctgcagtgt ccgtttctag agcacgagcc ggttcgggac aacaagggcc tggccagcag    1680
ggcccaggtc aacaagggcc aggacagcag ggtccttatg ggcccggcgc aagcgcagca    1740
gctgcggccg ctggtggcta tggtcctggc tccggtcaac agggcccttc gcaacaaggt    1800
cccgggcagc aaggtcctgg tggccagggt ccctacgggc cggggcgag tgcggcagca    1860 gccgctgcag gcggttatgg tccaggaagc ggacagcaag gtccgggagg tcaaggtccg    1920
tatggcccag gctctagcgc ggctgccgct ccgcgggtg caacggacc agggagcgga    1980 caacagggcg cggacaaca gggtccagga cagcaaggcc caggggcgtc ggcggctgca    2040
gcggcggccg gaggctatgg acccggctca ggacaacagg gaccgggtca acaaggaccc    2100
ggtggccaag gcccctatgg cccgggcgcc agcgcgccg cagccgccgc gggcgggtac    2160
ggccccggta gcggccaggg accaggtcag caggggccag gaggtcaggg cccatacggt    2220
ccgggcgcat ccgcggcggc ggcagcggca ggtggctacg gtcccggaag cggccaacag    2280
gggccagggc aacaaggacc aggacaacaa ggtcctgggg gccaaggacc gtatggacca    2340
ggagcatcag ctgcagccgc ggcagctggc ggttacggtc caggctacgg ccagcagggt    2400
ccgggtcagc agggaccggg aggccagggg ccttatggcc ctggcgcttc cgcagccagt    2460
gccgcttctg gaggatacgg gccgggaagc ggtcagcaag gcctggccaa caaggacct    2520 ggaggccaag ggcctacgg cccaggagcc tcggcagccg cagctgccgc aggtgggtat    2580
gggccaggta gcgggcaaca agggccgggt cagcaaggac cggggcaaca gggacctggg    2640
cagcaaggac ccgggggtca aggcccgtac ggacctggtg cgtctgcagc tgctgctgcg    2700
gctggtggat atggtccggg atcggggcag cagggtcccg gtcagcaggg ccctggtcag    2760
caagggccag ccaacaggg acccggacaa caaggcccgg tcaacaggg tcctggacag    2820 caggggccgg ccaacaagg ccctgggcaa caggtccgg ggggacaggg ggcctatggg    2880
cctggcgcat ctgccgccgc tggcgcagcc ggtgggtacg ggcctgggtc aggtcaacag    2940
gggcctggtc aacaaggccc cgggcaacag ggccccggcc agcaaggtcc agggcagcag    3000
ggcccgggac agcaagggcc tggacaacag gggcccggac agcaggacc ttacgggccc    3060 ggtgcgagcg cagcggccgc cgccgcaggg ggatatggcc ccggatcggg ccagcaggga    3120
ccaggccagc aaggacctgg ccaacaggc ccgggggtc aggggccgta tggtcccggc    3180
gctgcaagtg ctgcagtgtc cgttggaggt tacgcccctc agtcttcgtc tgttccggtg    3240
gcgtccgcag ttgcgagtag actgtcttca cctgctgctt catcgcgagt atcgagcgct    3300
gtttcgtctc ttgtctcgtc gggtcccacg aaacatgccg cccttcaaa tacgatttca    3360 tctgtagtgt cccaagttag tgcaagtaac ccggggttat ccggatgcga cgttctcgtt    3420
caggcactcc tagaagtagt atccgcgttg gtgagcatct tataa               3465
```

<210> SEQ ID NO 8
<211> LENGTH: 20
<212> TYPE: DNA
<213> ORGANISM: Artificial
<220> FEATURE:

```
<223> OTHER INFORMATION: T7 promoter primer

<400> SEQUENCE: 8
taatacgact cactataggg                                                20

<210> SEQ ID NO 9
<211> LENGTH: 27
<212> TYPE: DNA
<213> ORGANISM: Artificial
<220> FEATURE:
<223> OTHER INFORMATION: Rep Xba I primer

<400> SEQUENCE: 9
tctagaaacg dacactgcag cacttgc                                        27

<210> SEQ ID NO 10
<211> LENGTH: 28
<212> TYPE: DNA
<213> ORGANISM: Artificial
<220> FEATURE:
<223> OTHER INFORMATION: Xba I Rep primer

<400> SEQUENCE: 10
tctagagcac gagccggttc gggacaac                                       28

<210> SEQ ID NO 11
<211> LENGTH: 19
<212> TYPE: DNA
<213> ORGANISM: Artificial
<220> FEATURE:
<223> OTHER INFORMATION: T7 terminator primer

<400> SEQUENCE: 11
gctagttatt gctcagcgg                                                 19

<210> SEQ ID NO 12
<211> LENGTH: 5
<212> TYPE: PRT
<213> ORGANISM: Artificial
<220> FEATURE:
<223> OTHER INFORMATION: REP6-U1
<220> FEATURE:
<221> NAME/KEY: UNSURE
<222> LOCATION: (1)..(5)
<223> OTHER INFORMATION: Xaa at position 4 or 5 is any one of amino
      acids, in particular, it  preferably is Ala, Ser, Tyr, Gln, Val,
      Leu or Ile, it more preferably is Ala, Ser, Tyr, Gln or Val.

<400> SEQUENCE: 12

Gly Pro Gly Xaa Xaa
1               5

<210> SEQ ID NO 13
<211> LENGTH: 5
<212> TYPE: PRT
<213> ORGANISM: Artificial
<220> FEATURE:
<223> OTHER INFORMATION: REP6-U2
<220> FEATURE:
<221> NAME/KEY: UNSURE
<222> LOCATION: (1)..(5)
<223> OTHER INFORMATION: Xaa at position 5 is any one of amino acids,
      in particular, it preferably is Ala, Ser, Tyr, Gln, Val, Leu or
      Ile, it more preferably is Ala, Ser, Tyr, Gln or Val.
```

```
<400> SEQUENCE: 13

Gly Pro Gly Gly Xaa
1               5
```

POLAR SOLVENT SOLUTION AND PRODUCTION METHOD THEREOF

TECHNICAL FIELD

The present invention relates to a polar solvent solution that can keep its viscosity high and production methods thereof.

BACKGROUND ART

Polar solvents such as dimethylsulfoxide (DMSO) can dissolve substances such as polymers easily, so they are used for acrylic fiber polymerization and acrylic fiber spinning solutions, or as solvents for polyimide polymerization, etc. The inventors of the present invention have proposed application of the polar solvents as solvents of polypeptides such as spider silk proteins and silk proteins in Patent Documents 1 and 2.

PRIOR ART DOCUMENTS

Patent Documents

Patent Document 1: JP 5427322 B
Patent Document 2: JP 5584932 B

DISCLOSURE OF INVENTION

Problem to be Solved by the Invention

However, polar solvent solutions (e.g., solutions in which polypeptides such as spider silk proteins and silk proteins are dissolved in dimethylsulfoxide (DMSO)) may have reduced viscosities depending on how they are handled. The polar solvent solutions still have room for improvement in terms of performing stable spinning and casting when used as dopes for spinning, film, etc.

The present invention provides a polar solvent solution that enables stable spinning and casting without lowering its viscosity when used as dopes for spinning, film, etc., and methods for producing the same.

Means for Solving Problem

The present invention relates to a polar solvent solution in which a solute containing a polyamino acid is dissolved in a polar solvent. The solution has a moisture content (moisture percentage) of less than 5 mass % based on 100 mass % of the solution.

The present invention also relates to a method for producing a polar solvent solution in which a solute containing a polyamino acid is dissolved in a polar solvent. The method includes: changing a moisture content of the solution to adjust a viscosity of the solution.

The present invention also relates to a method for producing a polar solvent solution in which a solute containing a polyamino acid is dissolved in a polar solvent. The method includes: reducing a moisture content of the solution to increase a viscosity of the solution.

Effect of the Invention

The polar solvent solution of the present invention in which a solute containing a polyamino acid is dissolved in a polar solvent has a moisture content of less than 5 mass %. By doing so, it is possible to prevent the viscosity of the solution from lowering significantly, and thus spinning and casting are stabilized when the solution is used as dopes for spinning, film, etc. The production method of the present invention includes changing a moisture content of a polar solvent solution in which a solute containing a polyamino acid is dissolved in a polar solvent, so as to adjust a viscosity of the solution. By doing so, it is possible to obtain a polar solvent solution that enables stable spinning and casting. Moreover, the production method of the present invention includes reducing a moisture content of the solution to increase a viscosity of the solution. By doing so, it is possible to obtain a polar solvent solution that enables stable spinning and casting.

DESCRIPTION OF THE INVENTION

Figure 1:
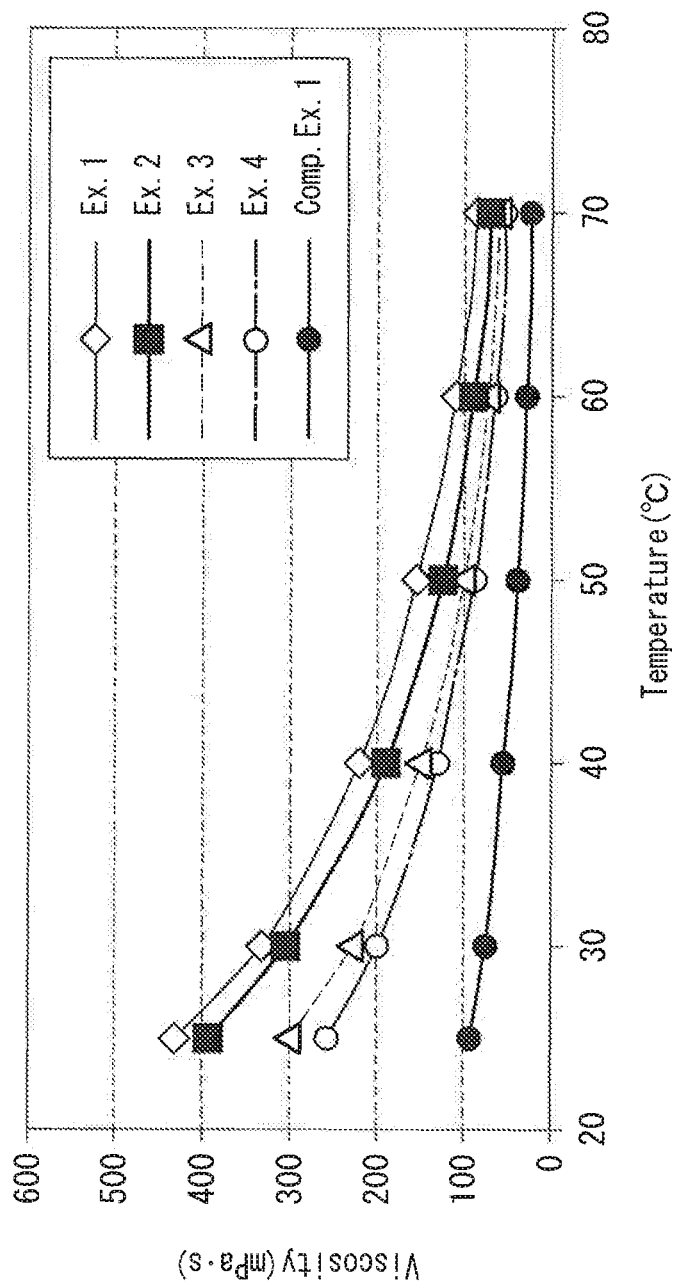
FIG. 1 is a graph showing a viscosity change with a temperature change in several examples and a comparative example of the present invention.

The inventors of the present invention found that polyamino acid (particularly polypeptide) itself, as well as a polar solvent solution in which a solute containing the polyamino acid is dissolved in polar solvent, readily absorbs moisture and lowers its viscosity. To cope with this problem, the polar solvent solution of the present invention in which a solute containing a polyamino acid is dissolved in a polar solvent has a moisture content of less than 5 mass % (0 mass % or more and less than 5 mass %) based on 100 mass % of the solution. The moisture content of the polar solvent solution is preferably 0 mass % or more and 3 mass % or less, more preferably 0 mass % or more and 1.5 mass % or less. Within this range, the polyamino acid (particularly polypeptide) in a swollen state is dissolved in the polar solvent, and the viscosity of the polar solvent solution is maintained high. In a case where the moisture content is 5 mass % or more, the viscosity of the polar solvent solution decreases significantly, and spinnability and casting properties decrease accordingly when the solution is used as dopes for spinning, film, etc. In the present specification, the polar solvent solution is also called a dope. The following mainly describes a case of using polypeptide, which is an exemplary polyamino acid.

It is preferred that the polar solvent to be used in the present invention contain at least one aprotic polar solvent selected from the group consisting of (i) dimethylsulfoxide (DMSO), N,N-dimethylformamide (DMF), (iii) N,N-dimethylacetamide (DMA), and (iv) N-methyl-2-pyrrolidone (NMP). This is because the aprotic polar solvents can dissolve solutes containing polypeptides easily. Examples of the polar solvent to be used in the present invention other than the solvents containing the above-described aprotic polar solvents include solvents containing protic polar solvents such as hexafluoroisopropanol (HFIP), formic acid, and various kinds of alcohols (e.g., lower alcohols having 1 to 6 carbon atoms such as methanol, ethanol, and 2-propanol). As the polar solvent, the ratio of the total amount of the at least one aprotic polar solvent selected from the group consisting of (i)-(iv) described above is desirably 10 to 100 mass %, based on 100 mass % of the polar solvent as a whole. Within this range, the solubility of the solutes containing polypeptides can be enhanced.

Any solute that contains a poly amino acid (particularly polypeptide) can be used as the solute of the present invention. In the present specification, the polyamino add refers to any polyamide compound polymerized through amide linkage between amino groups and carboxyl groups of amino acids. As the polyamino acid, the number of amino acids constituting the polyamide compound is preferably 15 or more, more preferably 20 or more, further preferably 30 or more, still further preferably 100 or more, and particularly preferably 500 or more, and preferably 6000 or less, more preferably 5000 or less, further preferably 3000 or less, and particularly preferably 2000 or less. The solute to be used in the present specification may be composed of, e.g., polyamino acid alone or contain one or more kinds of substances (e.g., carbohydrate, synthetic resin) other than the polyamino acid in combination with the polypeptide. Moreover, the solute to be used in the present specification may be composed of, e.g., polypeptide alone or contain one or more kinds of substances (e.g., carbohydrate, synthetic resin) other than the polypeptide in combination with the polypeptide. The polypeptide is preferably a structural protein, more preferably a structural protein including crystal regions. Such polypeptides can exhibit high strength and high toughness when formed into fibers, films, and the like. The structural protein refers to any protein involved in structures of living organisms, or any protein constituting structures created by living organisms. Examples of the structural protein include fibroin, sericin, collagen, keratin, elastin, and resillin.

The polypeptides are preferably fibroin such as spider silk proteins and silk proteins. Of these, spider silk proteins are particularly preferred because they have a high affinity for polar solvents and can be dissolved in the polar solvents easily.

When the polar solvent solution of the present invention is assumed to be 100 mass %, the concentration of the solute (e.g., spider silk protein) is desirably 2 to 50 mass %, further preferably 3 to 40 mass %, and particularly preferably 5 to 30 mass %. Within this range, the decrease or excessive increase of the viscosity of the polar solvent solution can be avoided effectively.

The polar solvent solution of the present invention, desirably in a state where undesired substances such as dust and bubbles have been removed, has a viscosity of preferably 10 to 100000 mPa·s, further preferably 15 to 20000 mPa·s, and particularly preferably 100 to 10000 mPa·s. The polar solvent solution within this viscosity range enables favorable wet spinning and film casting when used as dopes.

In the production method of the present invention, the viscosity of the polar solvent solution is adjusted by changing the moisture content of the polar solvent solution. Moreover, in the production method of the present invention, the viscosity of the polar solvent solution is increased by reducing the moisture content of the polar solvent solution. In these processes of manufacture, the moisture content of the polar solvent solution is adjusted to be preferably less than 5 mass %, more preferably 0 to 3 mass %, and further preferably 0 to 1.5 mass % based on 100 mass % of the solution. By doing so, it is possible to obtain a polar solvent solution that enables stable spinning and casting when used as dopes for spinning, film, etc.

In the production methods of the present invention, the adjustment for reducing the moisture content of the solution is achieved by, e.g., subjecting the solute or the solvent to heat drying or vacuum drying in advance, or adjusting the relative humidity of the atmosphere in at least one of the production and the storage of the solution, or vaporizing moisture of the produced solution by heating, or absorbing moisture using various kinds of moisture absorbents (moisture absorbent materials) such as zeolite, or combining these operations appropriately. Among the adjustment methods for reducing the moisture content of the solution described above, the method of drying the solute before dissolution in the solvent is favorably adopted. By doing so, the moisture content of the solution can be reduced more reliably and more efficiently. Moreover, in the case of changing the moisture content of the solution by adjusting the relative humidity of the atmosphere, it is advantageous that the relative humidity of the atmosphere in at least one of the production and the storage of the solution is kept at 1.3% RH or less. In order to keep the relative humidity of the atmosphere at 1.3% RH or less, it is preferred that processes such as the production and storage of the solution be carried out inside a dry room.

In the present invention, DMSO, which is suitably used as a polar solvent for dissolving a solute containing a polypeptide, is particularly advantageously used as, e.g., a solvent for dissolving a solute containing a spider silk protein. DMSO has a melting point of 18.4° C. and a boiling point of 189° C. DMSO has a much higher boiling point than hexafluoroisopropanol (HFIP) and hexafluroacetone (HFAc) having boiling points of 59° C. and −26.5° C., respectively, which have been used in conventional methods. Further, in view of the fact that DMSO has been used also in general industrial fields for acrylic fiber polymerization and acrylic fiber spinning solutions, and as solvents for polyimide polymerization, they are low cost substances with proven safety.

The spider silk proteins, which are exemplified as polypeptides to be contained in the solute of the present invention, are not limited particularly as long as they are natural spider silk proteins or proteins derived from or analogous to (hereinafter, simply referred to as "derived from") natural spider silk proteins. The proteins derived from natural spider silk proteins described herein are proteins having an amino acid sequence similar to or analogous to any of repetitive sequences of amino acids of natural spider silk proteins, examples of which includes variants, analogs, and derivatives of recombinant spider silk proteins and natural spider silk proteins. The spider silk proteins are preferably major dragline silk proteins produced in major ampullate glands of spiders or spider silk proteins derived therefrom, in terms of excellent tenacity Examples of the major dragline silk proteins include major ampullate spidroins MaSp1 and MaSp2 derived from *Nephila clavipes*, and ADF3 and ADF4 derived from *Arantius diadematus*, etc.

The spider silk proteins may be minor dragline silk proteins produced in minor ampullate glands of spiders or spider silk proteins derived therefrom. Examples of the minor dragline silk proteins include minor ampullate spidroins MiSp1 and MiSp2 derived from *Nephila clavipes*.

Other than these, the spider silk proteins may be flagelliform silk proteins produced in flagelliform glands of spiders or spider silk proteins derived therefrom. Examples of the flagelliform silk proteins include flagelliform silk proteins derived from *Nephila clavipes*, etc.

Examples of the spider silk proteins (polypeptides) derived from major dragline silk proteins include recombinant spider silk proteins containing two or more units of an amino acid sequence represented by the formula 1: REP1−

REP2 (1), preferably recombinant spider silk proteins containing four or more units thereof, and more preferably recombinant spider silk proteins containing six or more units thereof. In the recombinant spider silk proteins, units of the amino add sequence represented by the formula (1): REP1–REP2 (1) may be the same or different from each other.

In the formula (1), the REP1 represents a polyalanine region mainly constituted by alanine and expressed as (X1)p, and preferably the REP1 represents polyalanine. Here, p is not particularly limited, but preferably an integer of 2 to 20, more preferably an integer of 4 to 12. X1 represents alanine (Ala), serine (Ser), or glycine (Gly). The total number of alanine residues in the polyalanine region expressed as (X1)p is preferably 80% or more, more preferably 85% or more with respect to the total number of amino acid residues in the region. In the REP1, the number of alanine residues arranged in succession is preferably 2 or more, more preferably 3 or more, further preferably 4 or more, and particularly preferably 5 or more. Further, in the REP1, the number of alanine residues arranged in succession is preferably 20 or less, more preferably 16 or less, further preferably 12 or less, and particularly preferably 10 or less. In the formula (1), the REP2 is an amino acid sequence composed of 10 to 200 amino acid residues. The total number of glycine, serine, glutamine, proline and alanine residues contained in the amino acid sequence is 40% or more, preferably 50% or more, and more preferably 60% or more with respect to the total number of amino add residues contained therein.

The REP1 corresponds to a crystal region in a fiber where a crystal β sheet is formed, and the REP2 corresponds to an amorphous region in a fiber where flexibility is high and most of the parts lack regular configurations. Further, the [REP1–REP2] corresponds to a repeating region (repetitive sequence) composed of the crystal region and the amorphous region, which is a characteristic sequence of dragline silk proteins.

Examples of the recombinant spider silk proteins containing two or more units of the amino acid sequence represented by the formula 1: REP1–REP2 (1) are recombinant spider silk proteins derived from ADF3 having an amino acid sequence represented by any of SEQ NO: 1, SEQ NO: 2 and SEQ ID NO: 3. The amino acid sequence represented by SEQ ID NO: 1 is an amino acid sequence obtained by the following mutation: in an amino acid sequence of ADF3 to the N-terminal of which has been added an amino acid sequence (SEQ IT) NO: 4) composed of a start codon, His 10-tag and HRV3C Protease (Human rhinovirus 3C Protease) recognition site, $1^{st}$ to $13^{th}$ repetitive regions are about doubled and the translation ends at the $1154^{th}$ amino acid residue. The amino acid sequence represented by SEQ ID NO: 2 is an amino acid sequence obtained by adding the amino acid sequence (SEQ ID NO: 4) composed of a start codon, His 10-tag and HRV3C Protease (Human rhinovirus 3C Protease) recognition site, to the N-terminal of a partial amino acid sequence of ADF3 (NCBI Genebank Accession No.: AAC47010, GI: 1263287) obtained from the NCBI database. The amino acid sequence represented by SEQ ID NO: 3 is an amino acid sequence obtained by the following mutation: in an amino acid sequence of ADF3 to the N-terminal of which has been added the amino acid sequence (SEQ ID NO: 4) composed of a start codon, His 10-tag and HRV3C Protease (Human rhinovirus 3C Protease) recognition site, $1^{st}$ to $13^{th}$ repetitive regions are about doubled. Further, the recombinant spider silk proteins containing two or more units of the amino acid sequence represented by the formula 1: REP1–REP2 (1) may be spider silk proteins that are composed of an amino acid sequence represented by any of SEQ ID NO: 1, SEQ ID NO: 2 and SEQ ID NO: 3 in which one or more amino acids have been substituted, deleted, inserted and/or added and that have repeating regions composed of the crystal region and the amorphous region.

Examples of the spider silk proteins (polypeptides) derived from minor dragline silk proteins are recombinant spider silk proteins containing an amino acid sequence represented by the formula 2: REP3–REP4–REP5 (2). In the formula 2, the REP 3 indicates an amino acid sequence represented by (Gly-Gly-Z)m, the REP4 indicates an amino acid sequence represented by (Gly-Ala)l, and the REP5 indicates an amino acid sequence represented by (Ala)r. In the REP3, Z indicates any one of amino adds, particularly, it is preferably an amino acid selected from the group consisting of Ala, Tyr and Gln. Further, in the REP3, m is preferably 1 to 4. In the REP4, l is preferably 0 to 4. In the REP 5, r is preferably 1 to 6.

Among spider silks, the minor dragline silk is wound spirally from the center of a spider net, and used as a reinforcement of the net and a yarn to wrap a captured prey. The minor dragline silk is inferior to the major dragline silk in tensile strength, but is known to have high stretchability. The reason for this is considered to be as follows: in the minor dragline silk, since many crystal regions are composed of regions where glycine and alanine are arranged alternately in succession, the hydrogen bonds of the crystal regions weaken easily as compared with the major dragline silk whose crystal regions are composed only of alanine.

Examples of the recombinant spider silk proteins (polypeptides) derived from flagelliform silk proteins include recombinant spider silk proteins containing an amino acid sequence represented by the formula 3: REP6 (3). In the formula 3, the REP 6 indicates an amino acid sequence represented by (U1)n or (U2)n. In the REP6, U1 indicates an amino acid sequence represented by Gly-Pro-Gly-X-X (SEQ ID NO: 12), and U2 indicates an amino acid sequence represented by Gly-Pro-Gly-Gly-X (SEQ ED NO: 13). In the U1 and U2, X indicates any one of amino adds, particularly, it is preferably an amino acid selected from the group consisting of Ala, Ser, Tyr, Gin, Val, Leu, and Ile, more preferably an amino acid selected from the group consisting of Ala, Ser, Tyr, Gln, and Val. A plurality of X may be the same or different from each other. In the REP6, n indicates a number of 4 or larger, preferably 10 or larger, and more preferably 20 or larger.

Among spider silks, the flagelliform silk does not have crystal regions but has repeating regions composed of the amorphous region, which is a major characteristic of the flagelliform silk. It is considered that since the major dragline silk and the like have repeating regions composed of the crystal region and the amorphous region, they have both high stress and stretchability. Meanwhile, regarding the flagelliform the stress is inferior to that of the major dragline silk but the stretchability is high. The reason for this is considered to be that the flagelliform silk is composed mostly of the amorphous region.

The recombinant spider silk proteins (polypeptides) can be produced using a host that has been transformed by an expression vector containing a gene encoding a natural spider silk protein subjected to recombination. A method for producing a gene is not limited particularly, and it may be produced by amplifying a gene encoding a natural spider silk protein from a cell derived from spiders by a polymerase chain reaction (PCR) or the like, and cloning it, or may be synthesized chemically. A method for chemically synthesizing a gene also is not limited particularly, and it can be synthesized as follows, for example: based on information of amino acid sequences of natural spider silk proteins obtained from the NCBI web database or the like, oligonucleotides that have been synthesized automatically with AKTA oligopilot plus 10/100 (GE Healthcare Japan Corporation) are linked by PCR or the like. At this time, in order to facilitate purification and observation of protein, a gene may be synthesized that encodes a protein having the above-described amino acid sequence to the N-terminal of which has been added an amino acid sequence composed of a start codon and His 10-tag. Examples of the expression vector include a plasmid, a phage, a virus and the like that can express protein based on a DNA sequence. The plasmid-type expression vector is not limited particularly as long as it allows a target gene to be expressed in a host cell and it can amplify itself. For example, in the case of using *Escherichia coli* Rosetta (DE3) as a host, a pET22b(+) plasmid vector, a pCold plasmid vector and the like can be used. Among these, in terms of productivity of protein, it is preferable to use the pET22b(+) plasmid vector. Examples of the host include animal cells, plant cells, microbes, etc.

EXAMPLES

Hereinafter, the present invention will be described in further detail by way of examples. Note that the present invention is not limited to the following examples.
<Various Measurement Methods>
(1) Viscosity: The viscosities of polar solvent solutions (dopes) were measured using an EMS viscometer (EMS-01S) manufactured by Kyoto Electronics Manufacturing Co., Ltd.
(2) Relative humidity: The temperature and the dew-point temperature of an experiment environment were measured to calculate the relative humidity of the environment using a known calculation.
(3) Moisture percentage of dope: The moisture percentages of dopes were measured using a Hybrid Karl Fischer Moisture Titrator (MKH-700) manufactured by Kyoto Electronics Manufacturing Co., Ltd.

Examples 1-4, Comparative Example 1

1. Preparation of Spider Silk Proteins
<Gene Synthesis>
(1) Gene Synthesis of ADF3Kai
A partial amino acid sequence of ADF3 (GI: 1263287), which is one of two principal dragline silk proteins of *Araneus diadematus*, was obtained from the NCBI web database, and synthesis of a gene encoding an amino acid sequence (SEQ ID NO: 2) was outsourced to GenScript, Inc. The amino acid sequence (SEQ ID NO: 2, is an amino add sequence obtained by adding an amino add sequence (SEQ ID NO: 4) composed of a start codon, His 10-tag and HRV3C Protease (Human rhinovirus 3C Protease) recognition site, to the N-terminal of said partial amino add sequence of ADF3. As a result, a pUC57 vector to which a gene of ADF3Kai having a base sequence represented by SEQ ID NO: 5 had been introduced was obtained (having an Nde I site immediately upstream of 5' terminal of the gene and an Xba I site immediately downstream of 5' terminal thereof). Thereafter, the gene was subjected to a restriction enzyme treatment with Nde I and EcoR I, and recombined into a pET22b(+) expression vector.

(2) Gene Synthesis of ADF3Kai-Large
The half of the gene sequence of ADF3Kai on the 5' side (hereinafter, referred to as a sequence A) was amplified by the PCR reaction using ADF3Kai as a template, and a T7 promoter primer (SEQ IT) NO: 8) and a Rep Xba I primer (SEQ ID NO: 9). The obtained DNA fragment of the sequence A was recombined into a pUC118 vector that had been subjected to the restriction enzyme treatment with Nde I and Xba I in advance using a Mighty Cloning Kit (manufactured by TAKARA BIO Similarly the half of the gene sequence of ADF3Kai on the 3' side (hereinafter, referred to as a sequence B) was amplified by the PCR reaction using ADF3Kai as a template, and an Xba I Rep primer (SEQ 11) NO: 10) and a T7 terminator primer (SEQ ID NO: 11). The obtained DNA fragment of the sequence B was recombined into a pUC118 vector that had been subjected to the restriction enzyme treatment with Xba I and EcoR I in advance using the Mighty Cloning Kit (manufactured by TAKARA BIO INC.). The pUC118 vector to which the sequence A had been introduced and the pUC118 vector to which the sequence B had been introduced were subjected to the restriction enzyme treatment with Nde I, Xba I and Xba I, EcoR I, respectively, and target DNA fragments of the sequences A and B were purified by gel cut. The DNA fragments A, B and the pET22b(+) that had been subjected to the restriction enzyme treatment with Nde I and EcoR I in advance were subjected to a ligation reaction and transformed into *Escherichia coli* DH5a. After confirmation of the insertion of the target DNA fragments by a colony PCR using a T7 promoter primer and a T7 terminator primer, plasmid was extracted from a colony where a target band size (3.6 kbp) was obtained, and the entire base sequence was checked by a sequence reaction using a 3130×1 Genetic Analyzer (Applied Biosystems). Consequently; the construction of a gene of ADF3Kai-Large represented by SEQ ID NO: 6 was confirmed. The amino acid sequence of ADF3Kai-Large is as represented by SEQ ID NO: 3.

(3) Gene Synthesis of ADF3Kai-Large-NRSH1
With a pET22b(+) vector to which the gene of ADF3Kai-Large obtained above had been introduced used as a template, through site-directed mutagenesis using a PrimeSTAR Mutagenesis Basal Kit (manufactured by TAKARA BIO INC.), a codon GGC corresponding to the 1155th amino acid residue, i.e., glycine (Gly), in the amino acid sequence of ADF3Kai-Large (SEQ ID NO: 3) was mutated into a stop codon TAA, and a gene of ADF3Kai-Large-NRSH1 represented by SEQ ID NO: 7 was constructed on the pET22b(+). The accuracy of the introduction of the mutation was checked by the sequence reaction using the 3130×1 Genetic Analyzer (Applied Biosystems). The amino acid sequence of ADF3Kai-Large-NRSH1 is as represented by SEQ NO: 1.
<Expression of Protein>
The pET22b(+) expression vector containing the gene sequence of ADF3Kai-Large-NRSH1 was transformed into *Escherichia coli* Rosetta (DE3). The obtained single colony was incubated for 15 hours in 2 ml of an LB culture medium containing ampicillin. Thereafter, 1.4 ml of the culture solution was added to 140 ml of an LB culture medium containing ampicillin, and incubated to an $OD_{600}$ of 3.5 under the conditions of 37° C. and 200 rpm. Next, the culture solution with the $OD_{600}$ of 3.5 was added to 7 L of a 2×YT culture medium containing ampicillin, together with 140 nil of 50% glucose, and incubated further to the $OD_{600}$ of 4.0. Thereafter, isopropyl-β-thiogalactopyranoside (IPTG) was added to the obtained culture solution with the $OD_{600}$ of 4.0 so that the final concentration would be 0.5 mM, thereby inducing the expression of protein. After a lapse of two hours from the addition of IPTG, the culture solution was centrifuged and bacterial cells were collected. Protein solutions prepared from the culture solution before the addition of IPTG and after the addition of IPTG were each electrophoresed in a polyacrylamide gel. Consequently, a target band size (about 101.1 kDa) was observed with the addition of IPTG, and the expression of the target protein was confirmed.

Purification (1) About 50 g of bacteria cells of the *Escherichia coli* expressing the ADF3Kai-Large-NRSH1 protein and 300 ml of a buffer solution AI (20 mM Tris-HCl, pH 7.4) were placed in a centrifuge tube (1000 ml). After dispersing the bacteria cells with a mixer ("T18 basic ULTRA TURRAX" manufactured by IKA, level 2), the dispersion was centrifuged (11,000 g, 10 minutes, room temperature) with a centrifuge ("Model 7000" manufactured by Kubota Corporation), and a supernatant was discarded.

(2) To a precipitate (bacteria cells) obtained by the centrifugation, 300 ml of the buffer solution AI and 3 ml of 0.1 M PMSF (dissolved by isopropanol) were added. After dispersing the precipitate for 3 minutes with the mixer (level 2) manufactured by IKA, the bacteria cells were disrupted repeatedly for three times using a high-pressure homogenizer ("Panda Plus 2000" manufactured by GEA Niro Soavi).

(3) To the disrupted bacterial cells, 300 ml of a buffer solution B (50 mM Tris-HCL, 100 mM NaCl, pH 7.0) containing 3 w/v % of SDS was added. After dispersing well the bacterial cells with the mixer (level 2) manufactured by IKA, the dispersion was stirred for 60 minutes with a shaker (manufactured by TAITEC CORPORATION, 200 rpm, 37° C.). Thereafter, the stirred dispersion was centrifuged (11,000 g. 30 minutes, room temperature) with the centrifuge manufactured by Kubota Corporation, and a supernatant was discarded, whereby SDS washing granules (precipitate) were obtained.

(4) The SDS washing granules were suspended in a DMSO solution containing 1M lithium chloride so that the concentration would be 100 mg/nil, and heat-treated for 1 hour at 80° C. Thereafter, the heated suspension was centrifuged (11,000 g, 30 minutes, room temperature) with the centrifuge manufactured by Kubota Corporation, and the supernatant was collected.

(5) Ethanol in an amount three times greater than that of the collected supernatant was prepared. The collected supernatant was added to the ethanol, and left to stand still for 1 hour at room temperature. Thereafter, the resultant was centrifuged (11,000 g, 30 minutes, room temperature) with the centrifuge manufactured by Kubota Corporation to collect aggregated protein. Next, a process of washing aggregated protein using pure water and a process of collecting aggregated protein by centrifugation were repeated three times, and then moisture was removed by a freeze dryer to collect freeze-dried powder. The purification degree of the target protein ADF3Kai-Large-NRSH1 (about 56.1 kDa) in the obtained freeze-dried powder was checked by analyzing images of the results of polyacrylamide gel electrophoresis (CBB staining) of said protein powder using Totallab (non-linear dynamics Ltd.). As a result, the purification degree of ADF3Kai-Large-NRSH1 was about 85%.

2. Adjustment of Dopes and Viscosity Measurement

The spider silk protein (powder) obtained above was subjected to vacuum drying (bone dry), and the spider silk protein in the absolute dry state was added to five DMSO solvents of a predetermined amount prepared beforehand so that the concentration of the protein of the respective solvents would be 15 mass %. Different amounts of pure water were added and mixed into four of the five DMSO solvents containing the spider silk protein to prepare five kinds of dopes having different moisture contents (moisture percentages) as indicated in Table 1 below. The dopes with a moisture content of 0 mass %, 0.75 mass %, 1.5 mass %, and 3 mass % are dopes of Examples 1, 2, 3, and 4, respectively. The dope with a moisture content of 5 mass % is a dope of Comparative Example 1. In the preparation of the five kinds of dopes of Examples 1-4 and Comparative Example 1, the spider silk protein was dissolved in the solvents for 5 hours using a shaker, and then dust and bubbles were removed from the solvents. This process was all performed in a dry room at a relative humidity of 1.3% RH or less. The storage was also in a dry room at a relative humidity of 1.3% RH or less. The viscosity change with temperature was tested for the dopes of Examples 1-4 and the dope of Comparative Example 1. Table 1 below and FIG. 1 show the results.

TABLE 1

| | | Viscosity (mPa · s) | | | | | |
|---|---|---|---|---|---|---|---|
| | Temperature (° C.) | 70 | 60 | 50 | 40 | 30 | 25 |
| Ex. 1 | H$_2$O, 0 mass % | 82 | 110 | 153 | 221 | 333 | 434 |
| Ex. 2 | H$_2$O, 0.75 mass % | 67 | 89 | 124 | 193 | 306 | 393 |
| Ex. 3 | H$_2$O, 1.5 mass % | 56 | 73 | 100 | 150 | 232 | 299 |
| Ex. 4 | H$_2$O, 3 mass % | 49 | 63 | 89 | 132 | 199 | 261 |
| Comp. Ex. 1 | H$_2$O, 5 mass % | 23 | 30 | 39 | 53 | 76 | 92 |

*Ex.: Example, Comp. Ex.: Comparative Example

As is clear from Table 1 and FIG. 1, the dopes of Examples 1-4 with a moisture content of less than 5 mass % had high viscosities regardless of the temperature, and the viscosity rise in accordance with the temperature drop was significant, as compared with the dope of Comparative Example 1 with a moisture content of 5 mass %. Further, as to the dopes of Examples 1-4, the viscosity was high as the moisture content was low, i.e., the dope of Example 1 with a moisture content of 0 mass % had the highest viscosity. Moreover, at a temperature of 25° C., which is close to room temperature, the viscosities of the dopes of Examples 1-4 were much higher than the viscosity of the dope of Comparative Example 1, specifically, they were 2.8 to 4.7 times the viscosity of the dope of Comparative Example 1. These results clearly indicate that the viscosities of the dopes can be increased by adjusting the moisture content of the dopes to be less than 5 mass %. It was also confirmed that spinning and casting can be stabilized with the dopes of Examples 1-4.

Examples 5-9

Figure 2:
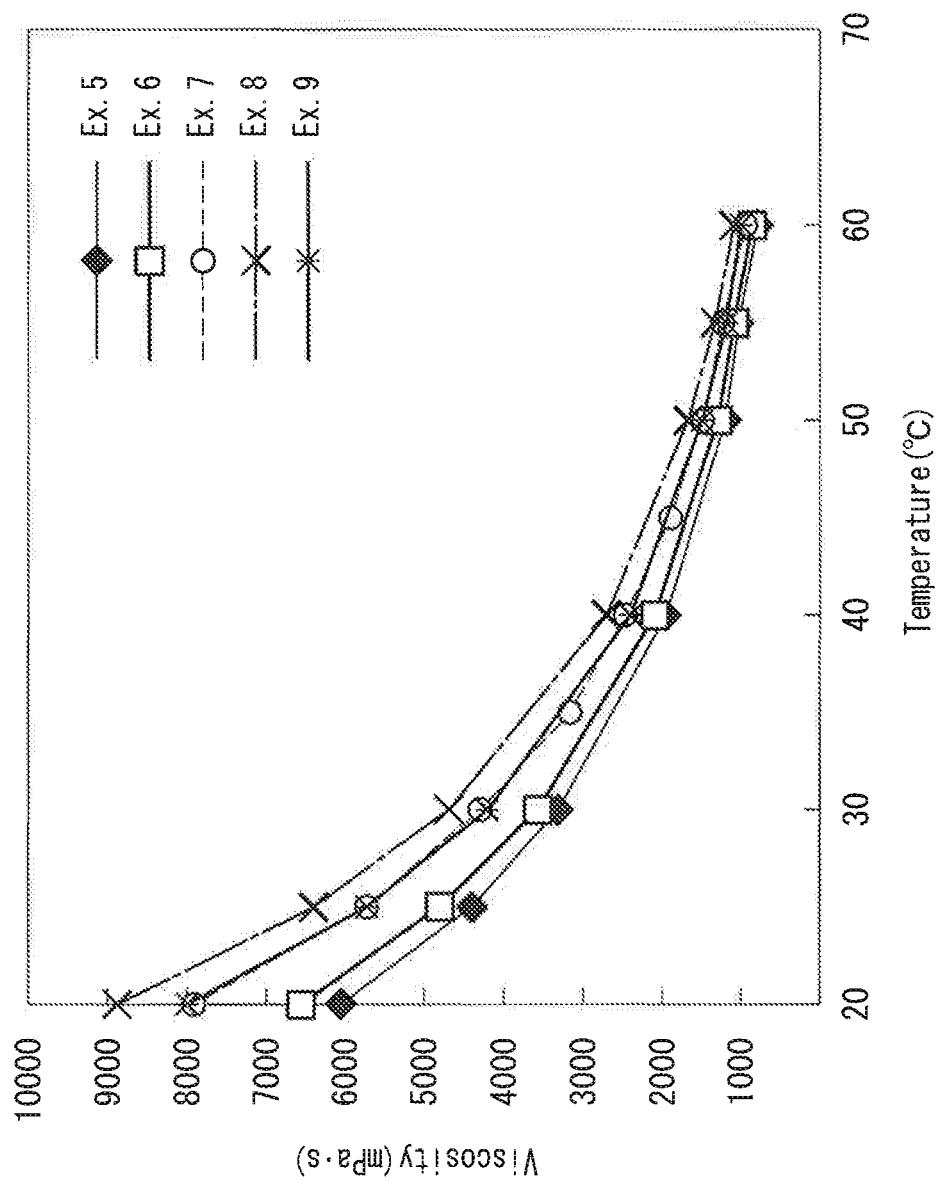
FIG. 2 is a graph showing a viscosity change when with or without humidity control and the concentration and temperature of protein are changed in other examples of the present invention.

This experiment was carried out to examine the viscosity change when with or without humidity control and the concentration and temperature of spider silk protein were changed. First, the spider silk protein (powder) obtained above was subjected to vacuum drying (bone dry), and the spider silk protein (powder) in the absolute dry state (moisture content: 0 mass %) was dissolved in DMSO solvents at concentrations indicated in Table 2 below in a dry room at a relative humidity of the atmosphere of 1.3% RH or less, so as to produce four kinds of dopes (Examples 5-8) having different concentrations of the spider silk protein. Then, the four kinds of dopes of Examples 5-8 were stored in a dry room at a relative humidity of 1.3% RH or less for 24 hours. Further, the spider silk protein (powder) in the absolute dry state was dissolved in a DMSO solvent at a concentration of 22.0 mass % in a general laboratory (in the atmosphere) without humidity control to produce a dope of Example 9. The dope of Example 9 was stored in a general laboratory without humidity control for 24 hours. The respective conditions of the experiment are shown in Table 2 below. A relationship between the temperature and the viscosity of the dopes of Examples 5-9 was examined. FIG. 2 shows the results.

TABLE 2

|  | Ex. 5 | Ex. 6 | Ex. 7 | Ex. 8 | Ex. 9 |
|---|---|---|---|---|---|
| Protein concentration (mass %) | 19.5 | 20.0 | 20.5 | 21.5 | 22.0 |
| With or without adjustment in dry room | With | With | With | With | Without |
| With or without storage in dry room | With | With | With | With | Without |

As indicated in FIG. 2, the relationship between the temperature and the viscosity of the dope of Example 9 (produced and stored in an environment without humidity control and having a protein concentration of 22.0 mass %) was substantially the same as that of the dope of Example 7 (produced and stored in the dry room and having a protein concentration of 20.5 mass %). The reason for this is considered to be that the moisture in the atmosphere was mixed into the dope of Example 9 during the production and storage. These results indicate that the viscosities of the dopes can be kept high by lowering the relative humidity of the atmosphere in the production and storage of the dopes to prevent the dopes from absorbing moisture.

(Reference Test 1)

Figure 3:
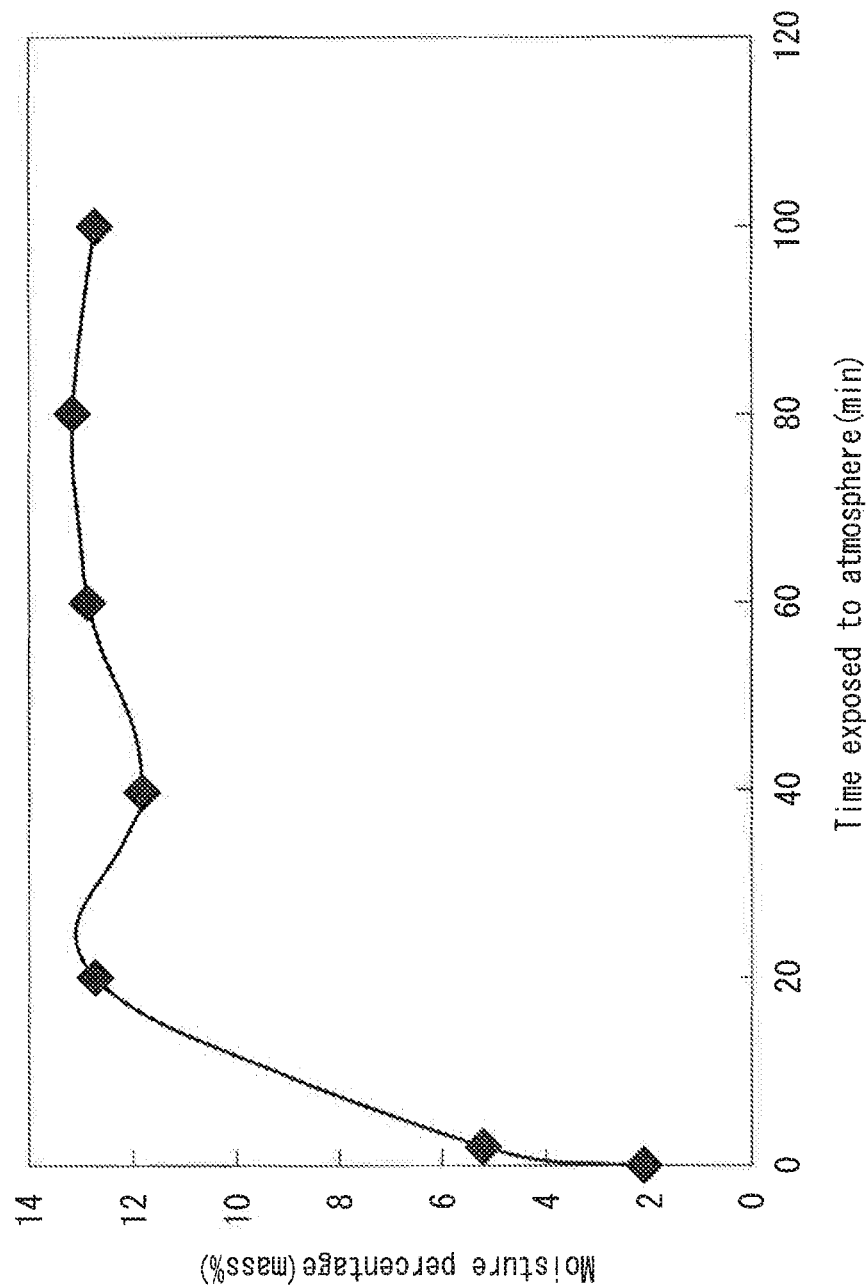
FIG. 3 is a graph showing a change in moisture percentage when spider silk protein (powder) in an absolute dry state is exposed to an atmosphere.

The spider silk protein (powder) obtained above was subjected to vacuum drying (bone dry), and the spider silk protein (powder) in the absolute dry state was exposed to an atmosphere at a temperature of 25° C. and a relative humidity of 72% RH to examine a change in moisture percentage. FIG. 3 shows the results. As is clear from FIG. 3, the moisture percentage of the spider silk protein (powder) in the absolute dry state reached about 13 mass % (equilibrium moisture regain) in about 20 minutes. This test result indicates that it is important for the spider silk protein (powder) to be subjected to vacuum drying to prepare dopes. Without the vacuum drying, the moisture adsorbed to the spider silk protein (powder) during the storage under the room temperature or an environment with high relative humidity is mixed into dopes directly (Reference Test 2)

The following test was performed to confirm that the lowering of the viscosity of the dope due to the mixing of moisture into the dope was not simply attributed the dilution of the dope with moisture. First, a dishwashing detergent having almost the same viscosity as that of the dope of Example 1 at 50° C. was prepared. Next, moisture was added to the dishwashing detergent so that the moisture content would be 3 mass % based on 100 mass % of the dishwashing detergent. Then, the viscosity of the dishwashing detergent at 50° C. was measured to determine a rate of change of viscosity before and after addition of moisture.

As a result, the viscosity of the dishwashing detergent at 50° C. before addition of moisture was 143 mPa·s, and the viscosity of the dishwashing detergent at 50° C. after addition of moisture was 133 mPa·s. A lowering rate of the viscosity of the dishwashing detergent at 50° C. due to addition of moisture was 7%. Meanwhile, the viscosity of the dope of Example 1 at 50° C. was 153 mPa·s, and the viscosity of the dope of Example 4 at 50° C. with a moisture content of 3 mass % by addition of moisture was 89 mPa·s. A lowering rate of the viscosity of the dope containing the spider silk protein at 50° C. due to addition of moisture was 42%. It was clearly recognized from these results that the lowering of the viscosity of the polar solvent solution containing polypeptide (e.g., spider silk protein) due to the mixing of moisture into the solution was not simply attributed to the dilution with moisture.

The following are considered as the reasons for the significant lowering of the viscosity of the polar solvent solution of polypeptide due to the mixing (inclusion) of moisture into the solution. Amino acids constituting molecules of protein (polypeptide) have various side chains. When water molecules enter the polar solvent solution of protein, hydrogen bonds are formed between the side chains of the protein molecules, and the protein molecules agglomerate. This decreases the solubility of the protein, and lowers the viscosity of the polar solvent solution of protein. Therefore, by removing water molecules from the polar solvent solution of protein, the agglomeration of the protein molecules can be avoided, and the solubility of the protein into the polar solvent solution can be enhanced, resulting in an increase in the viscosity of the polar solvent solution.

INDUSTRIAL APPLICABILITY

The polar solvent solution of the present invention is useful for wet spinning, film casting, gels, particles, mesh materials, and various types of moldings.

SEQUENCE LISTING FREE TEXT

SEQ ID NOS: 1-4, 12, 13 amino add sequences
SEQ ID NOS: 5-7 base sequences
SEQ ID NOS: 8-11 primer sequences

The invention claimed is:

1. A method for producing a polar solvent solution in which a solute containing a polyamino acid is dissolved in a polar solvent, comprising:
    changing a water content of the solution to adjust the viscosity of the solution,
    wherein the solution has a water content of less than 5% by mass based on 100% by mass of the solution, and
    the polar solvent comprises at least one selected from the group consisting of dimethylsulfoxide (DMSO), N,N-dimethylformamide (DMF), N,N-dimethylacetamide (DMA), and N-methyl-2-pyrrolidone (NMP).

2. A method for producing a polar solvent solution in which a solute containing a polyamino acid is dissolved in a polar solvent, comprising:
    reducing a water content of the solution to increase the viscosity of the solution,
    wherein the solution has a water content of less than 5% by mass based on 100% by mass of the solution, and
    the polar solvent comprises at least one selected from the group consisting of dimethylsulfoxide (DMSO), N,N-dimethylformamide (DMF), N,N-dimethylacetamide (DMA), and N-methyl-2-pyrrolidone (NMP).

3. The method for producing a polar solvent solution according to claim 1, wherein the polyamino acid is a polypeptide.

4. The method for producing a polar solvent solution according to claim 1, wherein the solute containing the polyamino acid is dried to reduce a water content of the solute, prior to dissolving the solute in the polar solvent.

5. The method for producing a polar solvent solution according to claim 1, wherein the water content of the solution is changed by adjusting a relative humidity of an atmosphere in the production and/or storage of the solution.

6. The method for producing a polar solvent solution according to claim 5, wherein the relative humidity of the atmosphere in the production and/or storage of the solution is adjusted to 1.3% RH or less.

7. The method for producing a polar solvent solution according to claim 2, wherein the polyamino acid is a polypeptide.

8. The method for producing a polar solvent solution according to claim 2, wherein the solute containing the polyamino acid is dried to reduce a water content of the solute, prior to dissolving the solute in the polar solvent.

9. The method for producing a polar solvent solution according to claim 2, wherein the water content of the solution is changed by adjusting a relative humidity of an atmosphere in the production and/or storage of the solution.

10. The method for producing a polar solvent solution according to claim 9, wherein the relative humidity of the atmosphere in the production and/or storage of the solution is adjusted to 1.3% RH or less.

11. The method for producing a polar solvent solution according to claim 1, wherein the solution exhibits at least one of the following viscosity properties (a) to (f):
    (a) a viscosity in a range from 100 to 434 mPa·s at 25° C.;
    (b) a viscosity in a range from 100 to 333 mPa·s at 30° C.;
    (c) a viscosity in a range from 100 to 221 mPa·s at 40° C.;
    (d) a viscosity in a range from 89 to 153 mPa·s at 50° C.;
    (e) a viscosity in a range from 63 to 110 mPa·s at 60° C.; and
    (f) a viscosity in a range from 49 to 82 mPa·s at 70° C.

12. The method for producing a polar solvent solution according to claim 2, wherein the solution exhibits at least one of the following viscosity properties (a) to (f):
    (a) a viscosity in a range from 100 to 434 mPa·s at 25° C.;
    (b) a viscosity in a range from 100 to 333 mPa·s at 30° C.;
    (c) a viscosity in a range from 100 to 221 mPa·s at 40° C.;
    (d) a viscosity in a range from 89 to 153 mPa·s at 50° C.;
    (e) a viscosity in a range from 63 to 110 mPa·s at 60° C.; and
    (f) a viscosity in a range from 49 to 82 mPa·s at 70° C.

* * * * *